US009420967B2

(12) United States Patent
Zand et al.

(10) Patent No.: US 9,420,967 B2
(45) Date of Patent: Aug. 23, 2016

(54) APPARATUS, SYSTEMS AND METHODS FOR DETERMINING TISSUE OXYGENATION

(71) Applicant: SURGISENSE CORPORATION, Bethesda, MD (US)

(72) Inventors: Jason M. Zand, Washington, DC (US); Gregory S. Fischer, Jamaica Plain, MA (US)

(73) Assignee: Surgisense Corporation, Bethesda, MD (US)

( * ) Notice: Subject to any disclaimer, the term of this patent is extended or adjusted under 35 U.S.C. 154(b) by 0 days.

(21) Appl. No.: 14/220,034

(22) Filed: Mar. 19, 2014

(65) Prior Publication Data
US 2014/0288386 A1    Sep. 25, 2014

Related U.S. Application Data

(60) Provisional application No. 61/803,451, filed on Mar. 19, 2013.

(51) Int. Cl.
*A61B 5/00*    (2006.01)
*A61B 5/1455*    (2006.01)
(Continued)

(52) U.S. Cl.
CPC .......... *A61B 5/14552* (2013.01); *A61B 5/0059* (2013.01); *A61B 5/1459* (2013.01); *A61B 5/14556* (2013.01); *A61B 5/6847* (2013.01); *A61B 5/01* (2013.01); *A61B 2505/05* (2013.01)

(58) Field of Classification Search
None
See application file for complete search history.

(56) References Cited

U.S. PATENT DOCUMENTS 4,476,870 A * 10/1984 Peterson .............. A61B 5/1459
                                                      250/458.1
4,515,165 A    5/1985 Carroll
(Continued)

FOREIGN PATENT DOCUMENTS

WO    WO-0018294 A1    4/2000
WO    2006/113394 A2    10/2006
(Continued)

OTHER PUBLICATIONS

PCT/US2014/031267: International Search Report and Written Opinion mailed Jul. 25, 2014.
(Continued)

*Primary Examiner* — William Thomson
*Assistant Examiner* — Bobby Soriano
(74) *Attorney, Agent, or Firm* — Venable LLP; Michele V. Frank; Trent B. Ostler

(57) ABSTRACT

A surgical instrument may be configured to sense a light re-emitting probe to resolve tissue oxygenation, the surgical instrument including: an optical emitter configured to excite the light re-emitting probe within an absorption band of the light re-emitting probe; an optical detector configured to receive the re-emitted light from the probe; and a signal processor configured to resolve the tissue oxygenation based on the received light. The surgical instrument can be a surgical stapler anvil or a flexible substrate having a tissue interfacing surface. Further, a monitoring device may be configured to map oxygenation of a tissue containing a light re-emitting probe, the monitoring device including: an optical emitter configured to excite the light re-emitting probe; at least one optical detector configured to receive the re-emitted light from the probe; and a signal processor that is configured to resolve the tissue oxygenation at multiple points to generate an oxygen map.

20 Claims, 17 Drawing Sheets

(51) Int. Cl.
*A61B 5/1459* (2006.01)
*A61B 5/01* (2006.01)

(56) References Cited

U.S. PATENT DOCUMENTS

| | | | |
|---|---|---|---|
| 4,947,850 A | 8/1990 | Venderkooi et al. | |
| 5,495,850 A * | 3/1996 | Zuckerman | G01N 21/6445 356/41 |
| 5,515,864 A * | 5/1996 | Zuckerman | G01N 21/6445 356/41 |
| 5,593,899 A * | 1/1997 | Wilson | A61B 5/0059 422/79 |
| 5,769,791 A | 6/1998 | Benaron et al. | |
| 5,833,603 A | 11/1998 | Kovacs et al. | |
| 5,837,865 A | 11/1998 | Vinogradov et al. | |
| 5,860,917 A | 1/1999 | Comanor et al. | |
| 5,987,346 A | 11/1999 | Benaron et al. | |
| 6,163,714 A | 12/2000 | Stanley et al. | |
| 6,165,741 A | 12/2000 | Wilson et al. | |
| 6,248,117 B1 * | 6/2001 | Blatter | 606/153 |
| 6,274,086 B1 | 8/2001 | Wilson et al. | |
| 6,362,175 B1 | 3/2002 | Vinogradov et al. | |
| 6,631,286 B2 | 10/2003 | Pfeiffer et al. | |
| 6,652,452 B1 | 11/2003 | Seifert | |
| 6,664,111 B2 | 12/2003 | Bentsen et al. | |
| 6,701,168 B1 | 3/2004 | Wilson et al. | |
| 6,975,898 B2 | 12/2005 | Seibel | |
| 7,341,557 B2 | 3/2008 | Cline et al. | |
| 7,364,574 B2 | 4/2008 | Flower | |
| 7,420,151 B2 | 9/2008 | Fengler et al. | |
| 7,532,325 B2 * | 5/2009 | Ahmed | G01J 3/02 356/317 |
| 7,575,890 B2 | 8/2009 | Wilson | |
| 7,722,534 B2 | 5/2010 | Cline et al. | |
| 7,918,559 B2 | 4/2011 | Tesar | |
| 8,082,015 B2 * | 12/2011 | Yodh | A61B 5/0059 356/406 |
| 8,118,206 B2 | 2/2012 | Zand et al. | |
| 8,185,176 B2 | 5/2012 | Mangat et al. | |
| 8,630,698 B2 | 1/2014 | Fengler et al. | |
| 8,647,605 B2 | 2/2014 | Mangat et al. | |
| 8,694,069 B1 * | 4/2014 | Kosa | A61B 5/1459 264/1.24 |
| 8,961,403 B2 | 2/2015 | Cline et al. | |
| 9,044,179 B2 * | 6/2015 | Wilson | A61B 5/14539 |
| 2003/0014064 A1 * | 1/2003 | Blatter | 606/153 |
| 2005/0131390 A1 | 6/2005 | Heinrich et al. | |
| 2005/0177035 A1 * | 8/2005 | Botvinick et al. | 600/347 |
| 2005/0240093 A1 * | 10/2005 | DeArmond | 600/372 |
| 2006/0239921 A1 | 10/2006 | Mangat et al. | |
| 2007/0299309 A1 | 12/2007 | Seibel | |
| 2008/0051646 A1 * | 2/2008 | Papkovsky et al. | 600/329 |
| 2008/0221648 A1 | 9/2008 | Flower | |
| 2008/0228037 A1 | 9/2008 | Cline et al. | |
| 2008/0285823 A1 | 11/2008 | Bakker | |
| 2008/0287736 A1 | 11/2008 | Yamazaki | |
| 2008/0291397 A1 | 11/2008 | Tesar | |
| 2008/0310583 A1 | 12/2008 | Truyen | |
| 2009/0054908 A1 | 2/2009 | Zand et al. | |
| 2009/0057543 A1 | 3/2009 | Ogikubo | |
| 2009/0203994 A1 | 8/2009 | Mangat et al. | |
| 2009/0216097 A1 * | 8/2009 | Wilson et al. | 600/327 |
| 2009/0234248 A1 * | 9/2009 | Zand | A61B 5/0031 600/587 |
| 2009/0303317 A1 | 12/2009 | Tesar | |
| 2010/0081895 A1 | 4/2010 | Zand | |
| 2010/0191081 A1 * | 7/2010 | Shahidi | 600/323 |
| 2010/0198010 A1 | 8/2010 | Cline et al. | |
| 2010/0202966 A1 * | 8/2010 | Gross | A61B 5/14532 424/9.1 |
| 2010/0210904 A1 | 8/2010 | Cline et al. | |
| 2010/0222673 A1 | 9/2010 | Mangat et al. | |
| 2011/0021889 A1 * | 1/2011 | Hoss | A61B 5/14532 600/310 |
| 2011/0104071 A1 * | 5/2011 | Lee et al. | 424/9.6 |
| 2011/0105869 A1 * | 5/2011 | Wilson et al. | 600/323 |
| 2011/0230715 A1 * | 9/2011 | Saito | 600/109 |
| 2012/0053433 A1 * | 3/2012 | Chamoun et al. | 600/324 |
| 2012/0053434 A1 * | 3/2012 | Saito | 600/324 |
| 2012/0116185 A1 | 5/2012 | Zand et al. | |
| 2012/0116192 A1 * | 5/2012 | Saito | 600/323 |
| 2012/0153188 A1 * | 6/2012 | Barrett | 250/461.1 |
| 2013/0102865 A1 | 4/2013 | Mandelis | |
| 2013/0224874 A1 | 8/2013 | Vinogradov et al. | |
| 2014/0194687 A1 | 7/2014 | Fengler et al. | |
| 2014/0308210 A1 | 10/2014 | Mangat et al. | |

FOREIGN PATENT DOCUMENTS

| | | |
|---|---|---|
| WO | 2007-050269 A2 | 5/2007 |
| WO | 2014-153428 A1 | 9/2014 |

OTHER PUBLICATIONS

Dunphy et al. "Oxyphor R and G2: phosphors for measuring oxygen by oxygen-dependent quenching of phosphorescense" Science Direct, Analytical Biochemistry 310, 2002, pp. 191-198.

Canadian Office Action and Examination Search Report issued in corresponding Canadian Patent Application No. 2,604,563, dated Oct. 24, 2014.

International Preliminary Report on Patentability in International Application No. PCT/US2006/013985, dated Mar. 10, 2009.

In the U.S. Patent and Trademark Office, First Action Interview Pilot Program Pre-Interview Communication re U.S. Appl. No. 14/679,707 dated Mar. 9, 2016, 23 pages.

* cited by examiner

US 9,420,967 B2

APPARATUS, SYSTEMS AND METHODS FOR DETERMINING TISSUE OXYGENATION

CROSS REFERENCE TO RELATED APPLICATIONS

This application claims priority to U.S. Provisional Patent Application No. 61/803,451, filed Mar. 19, 2013, which is hereby incorporated herein by reference in its entirety.

GOVERNMENT INTEREST

This invention was made with Government Support under National Institutes of Health grant no. CA153571. The Government has certain rights in the invention.

TECHNICAL FIELD

The present invention relates to systems, methods and medical devices for use with molecular probes for resolving tissue oxygenation. More particularly, the inventions are directed to systems, methods and medical devices with sensors used to detect properties of biological tissue and a system for resolving the information gathered by the sensors.

BACKGROUND

A living organism is made up of cells. Cells are the smallest structures capable of maintaining life and reproducing. Cells have differing structures to perform different tasks. A tissue is an organization of a great many similar cells with varying amounts and kinds of nonliving, intercellular substances between them. An organ is an organization of several different kinds of tissues so arranged that together they can perform a special function.

Surgery is defined as a branch of medicine concerned with diseases requiring operative procedures.

Although many surgical procedures are successful, there is always a chance of failure. Depending on the type of procedure these failures can result in pain, need for re-operation, extreme sickness, or death. At present there is no reliable method of predicting when a failure will occur. Most often the failure occurs after the surgical procedure has been completed. Failures of surgical procedures can take many forms. The most difficult failures to predict and avoid are those that involve biological tissue. This difficulty arises for three distinct reasons. Firstly, the properties that favor the continued function of biological tissue are very complex. Secondly, these properties are necessarily disrupted by surgical manipulation. Finally, the properties of biological tissues vary between patients.

During a surgical operation, a variety of surgical instruments are used to manipulate biological tissues. However, traditional surgical instruments do not have the ability to obtain information from biological tissues. Obtaining information from the biological tissues that surgical instruments manipulate can provide a valuable dataset that at present is not collected. For example, this dataset can quantitatively distinguish properties of tissues that will result in success or failure when adapted to specific patient characteristics.

What is needed are medical devices, systems and methods that can adapt to patient-specific characteristics that are of importance in avoiding surgical procedure failure.

BRIEF SUMMARY OF THE INVENTION

A surgical instrument is configured to sense a light re-emitting probe to resolve tissue oxygenation. The surgical instrument includes at least one optical emitter that is configured to excite the light re-emitting probe within an absorption band of the light re-emitting probe; at least one optical detector configured to receive the re-emitted light from the probe; and a signal processor that is configured to resolve the tissue oxygenation based on the received light.

The surgical instrument further includes an applicator configured to provide a target tissue with a medium, the medium containing the light re-emitting probe. The signal processor is configured to resolve the tissue oxygenation based in a lifetime of the re-emitted light. The surgical instrument is a surgical stapler anvil. The applicator is at least one injector that is configured to inject the medium into the target tissue. The surgical instrument further includes an interrogator instrument that is configured to interrogate the tissue. The surgical instrument is a flexible substrate having a tissue interfacing surface. The signal processor makes a determination of an operation success based on the resolution of the tissue oxygenation. The surgical instrument further includes a temperature sensor that is configured to detect a temperature of the tissue and at least one sensor configured to monitor interaction forces of at least one of compression pressure and tissue tension of the tissue. The probe is a phosphorescent probe that has multiple absorption wavelengths. The surgical instrument is communicatively coupled to a base station.

A surgical stapler anvil is configured to sense a light re-emitting probe to resolve tissue oxygenation. The surgical stapler anvil includes at least one optical emitter that is configured to excite the light re-emitting probe; at least one optical detector that is configured to receive the re-emitted light from the probe; and a signal processor that is configured to resolve the tissue oxygenation based on the received light.

The surgical stapler anvil is communicatively coupled to a base station. The signal processor makes a determination of an operation success based on the resolution of the tissue oxygenation. The surgical stapler anvil further includes a temperature sensor that is configured to detect a temperature of the tissue. The surgical stapler anvil further includes at least one sensor configured to monitor interaction forces of at least one of compression pressure and tissue tension of the tissue.

A monitoring device is configured to sense a light re-emitting probe to resolve tissue oxygenation. The monitoring device includes a flexible substrate having a tissue interfacing surface, the tissue interfacing surface containing (1) at least one optical emitter that is configured to excite the light re-emitting probe; and (2) at least one optical detector configured to receive the re-emitted light from the probe; and a signal processor that is configured to resolve the tissue oxygenation based on the received light.

The monitoring device includes at least one injector configured to inject a medium into target tissue, the medium containing the light re-emitting probe. The monitoring device is communicatively coupled to a base station. The signal processor makes a determination of an operation success based on the resolution of the tissue oxygenation. The monitoring device further includes a temperature sensor that is configured to detect a temperature of the tissue. The flexible substrate is configured to be one or more of: (1) affixed to skin and (2) affixed to an internal tissue. The monitoring device is at least partially bioabsorbable.

A monitoring device is configured to map oxygenation of a tissue containing a light re-emitting probe. The monitoring device includes at least one optical emitter that is configured to excite the light re-emitting probe; at least one optical detector configured to receive the re-emitted light from the probe; and a signal processor that is configured to resolve the tissue oxygenation at multiple points to generate an oxygen map.

The monitoring device further includes at least one injector configured to inject a medium into target tissue, the medium containing the light re-emitting probe. The monitoring device further includes a temperature sensor that is configured to detect a temperature of the tissue. The optical detector is at least one of a CCD array, a CMOS image sensor and a camera. The monitoring device is an endoscopic instrument. The monitoring device is ingestible.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

Figure 1A:
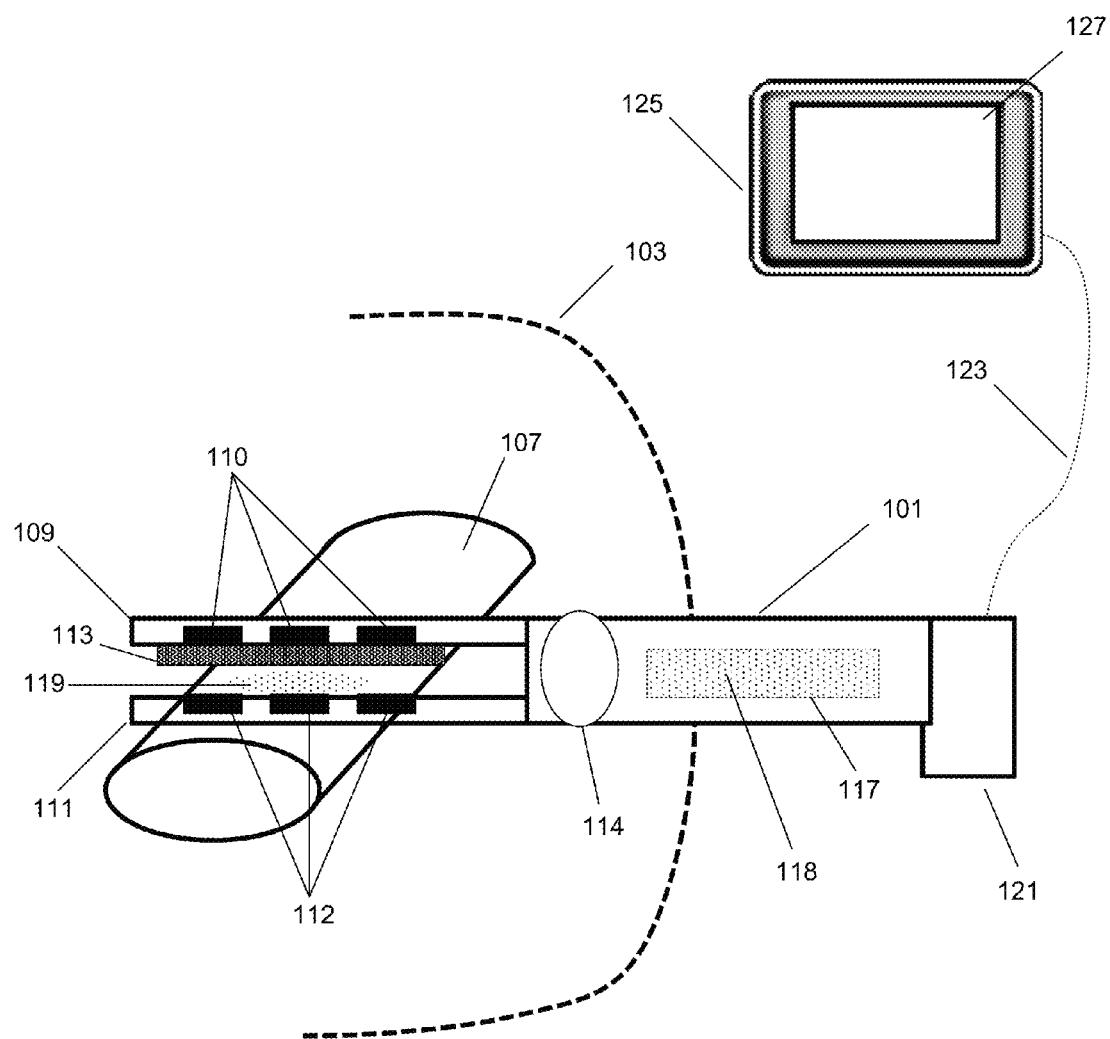
FIG. 1a shows a representative embodiment of a surgical instrument with sensing capabilities.

Each surgical procedure has the potential for failure. A common procedure in gastrointestinal surgery is a bowel resection—removing the affected portion of the bowel and then mechanically joining the ends of the remaining segments to re-establish bowel continuity. The mechanical connection of the free ends of bowel forms what is termed a surgical anastomosis. A surgical anastomosis is formed by either traditional techniques using suture material, or by contemporary techniques which may include utilizing surgical staplers or other surgical fastening device. A surgical stapler mechanically joins the bowel by firing a pattern of staples from a cartridge or housing through the two free ends of bowel against an anvil that ultimately forms a securing crimp on the opposing side. There are many embodiments of surgical staplers. Some staplers form linear staple patterns, while others form circular patterns. Some staplers incorporate functionality for cutting tissue. Many staplers have the ability to vary the gap between the base of the staple and the formed crimp.

Anastomotic failure is one of the most feared complications of gastrointestinal surgery due to the resultant morbidity and mortality. Failure of an anastomosis, or intestinal junction, can cause a spectrum of morbidities to the patient including local abscess formation—requiring procedural drainage, tumor recurrence, debilitating pain, dysfunctional defecation, and overwhelming bacterial sepsis resulting in death. Despite improvements in surgical technique, there remains limited ability to assess the anastomotic segment and predict outcome, and as a result anastomotic failure occurs at unacceptably high levels given the severe consequences. For example, in the performance of a low anterior resection (LAR) for excision of rectal cancer, anastomotic failure has been reported to occur in up to 30% of cases. One large multicenter, observational study of 2729 patients reported a leak rate of 14.3%. These anastomotic failures cause a significant and avoidable economic burden on the healthcare system, as well as an incalculable amount of pain, suffering, and hardship for the patients in which the failure occurs. The devastating consequences of an anastomotic failure are so severe that in the majority of cases surgeons performing a low anterior resection will opt to create a diverting ostomy at the time of resection to mitigate the risks of anastomotic failure. In the same study, 881 patients were given a temporary diverting ostomy while 128 patients developed a leak. Up to 85 percent of those patients underwent an additional surgical procedure to reverse the ostomy that provided questionable benefit. While a diverting ostomy can avoid the dire consequences of anastomotic failure, it does not prevent failure, and poses a risk for additional complications. The morbidity rate for a temporary ostomy is 20-30%. Complications include intestinal obstruction, torsion, dehydration, electrolyte imbalance, stomal refraction, and severe skin breakdown. Additionally, complications of ostomy closure occur in a third of patients. Furthermore an ostomy significantly compromises the lifestyle of the recovering patient.

There is neither a clinically practical apparatus that can quantitatively assess an anastomosis intra-operatively to determine the likelihood of failure, nor an objective set of criteria by which a surgeon can select those patients that would benefit from diverting ostomy. Nor is there a device that can help in determining the optimal placement of an anastomosis.

There exists a need for a device, system and methodology for reducing anastomotic failures through the analysis of target tissues before, during, and after the creation of an anastomosis. There also exists a need to objectively determine, at the time of surgery, those patients that would benefit from a diverting stoma procedure. There also exists a need to deliver adjunct therapies to the anastomotic site to optimize outcome.

To accomplish its goal, one embodiment of the present invention interrogates the tissue, prior to creation of an anastomosis, to enable the operative team to identify a suitable site based on quantitative criteria. Another embodiment couples to the desired stapling platform, which includes traditional off-the-shelf disposable surgical staplers, and uses an array of multimodality sensors to measure the viability of the tissues during the creation of the anastomosis. If tissue parameters are unsuitable for an anastomosis, the operative team can take corrective action, thus reducing the risk of anastomotic failure. At the conclusion of the formation of the anastomosis, the operative team can ensure tissue measures remain within acceptable range. If the measures are abnormal, the operative team can again take corrective action to improve outcome. Measurements may be made from the internal and/or external surface of the tissue.

One representative application of the present invention is in the treatment of colorectal cancer. Colorectal cancer (CRC) is the third most common cause of cancer for men and women in developed countries. Estimates predict that worldwide just under 1.2 million new cases of colorectal cancer were diagnosed in 2007. Rectal cancer accounts for approximately 27% of all colorectal cancers and presents the formidable challenge of ensuring a curative resection while maintaining acceptable function. The mainstay of treatment for rectal cancer is surgical resection—removing the affected portion of the bowel and performing an anastomosis on the ends of the remaining segments to re-establish bowel continuity. The end-to-end anastomosis (EEA) is most commonly performed using circular EEA staplers. As with any surgical procedure, resection of a rectal cancer can have complications. Amongst all of the possible complications the three most devastating to the patient in terms of morbidity and mortality are tumor recurrence, anastomotic leak and anastomotic stricture. Tumor recurrence can be reduced by: following oncologic principles of dissection, providing appropriate adjunctive chemotherapeutic, photodynamic, and radiation therapies, and preventing extra-luminal extravasation of residual intra-luminal neoplastic cells through anastomotic breakdown. Anastomotic failure has been anecdotally attributed to inadequate tissue perfusion and excessive tension at the anastomosis.

When determining the location of a rectal cancer the surgeon notes the distance of the tumor from the anal verge. The anal canal extends from 0-4 cm past the anal verge, and the rectum 4-19 cm. Surgically the rectum extends from the anal sphincters to the sacral promontory. The location of the cancer dictates the type of surgical procedure performed.

The primary goal of a curative resection is to remove all potential tissues harboring cancerous cells. To accomplish this goal, the surgical team aims to resect the tumor with a cancer free margin as well as the tumor's blood supply and draining lymphatic tissue. Tumors located in the upper rectum, greater than 12 cm from the anal verge, are regularly amenable to an anterior resection (AR). Those in the mid rectum, between 6-12 cm, are subject to a LAR with or without a total mesorectal excision (TME), and tumors in the lower rectum, 4-6 cm, are usually treated with an ultra-low anterior resection (ULAR), incorporating a TME, and either a colorectal or coloanal anastomosis. A total mesorectal excision is a technique that attempts to resect the rectum and all investing soft tissues en-bloc. This technique has been touted in the literature as having superior results in terms of minimizing local tumor recurrence, however it is speculated that the procedure has an inverse effect on leak rates due to the excision of the supplying vasculature to the anastomotic site. Every attempt is made to retain fecal continence, however those tumors involving the anal sphincters 0-4 cm are resected through a sphincter sacrificing abdominoperineal resection (APR). The present invention may be used to determine surgical resection margins and anastomosis location based upon sensor measurements. These measurements may be performed on the internal and/or external surface of the tissue and be interrogated as a single point or multiple locations.

As a secondary goal the surgical team strives to restore continuity of the bowel and ensuing fecal stream. To accomplish this goal an anastomosis is formed. Simply, an anastomosis is the surgical connection of two free ends of a tubular structure. When the continuity of the bowel cannot be restored, the fecal stream is diverted through a stoma, or opening, in the anterior abdominal wall through which the patient eliminates into an ostomy bag. There are two main reasons for stoma formation: resection of the anal sphincter complex, and diversion of the fecal stream. In a sphincter sacrificing procedure such as an APR, the patient is dependent on a permanent ostomy. With a sphincter sparing procedure such as a LAR, the fecal stream may diverted through a temporary ostomy in order to mitigate the risk of overwhelming sepsis resulting from fecal contents entering the abdominal cavity should there be a leak at the anastomosis. Most of the time a temporary stoma can be reversed within a few months after the initial operation through a separate procedure. The present invention may be used to assess the viability of the anastomosis and/or stoma based upon sensor measurements.

The scientific literature suggests that the cause of anastomotic failure is that inadequate tissue perfusion as a result of redefined vasculature, tissue interaction forces, edema, and tension result in a decrease of oxygen delivered to the anastomotic site. Without adequate oxygen delivery, efficient aerobic cell respiration cannot occur within the native cells leading to tissue degradation; collagen matrix cannot mature into strong collagen fibrils; and white blood cells cannot effectively fight bacterial invasion.

Normal healing of a gastrointestinal anastomosis follows an orderly reparative process. The inflammatory phase occurs immediately after disruption of the tissue and lasts 2-3 days. This phase is characterized by efflux of inflammatory cells into the wound. Increased permeability of vessels adjacent to the wound facilitates the delivery of target cells. Hemostasis is achieved through a platelet mediated fibrin based clot. Neutrophils initially dominate this phase with the goal of killing invading microbes. Macrophages appear next and secrete tissue growth factors that are paramount to progressive repair. The proliferative phase begins with the arrival of fibroblasts. The fibroblasts replace the provisional clot matrix with a loosely organized collagen framework. In this phase the anastomosis first weakens as collagen lysis initially outpaces synthesis. Colonic anastomoses lose up to 70% of their initial strength. Collagen synthesis requires hydroxylation of lysine and proline residues. Cofactors essential for this process are oxygen, ferrous iron, Vitamin C, and alpha-ketoglutarate. Angiogenesis begins during this stage to increase oxygen and nutrient delivery to meet the increased metabolic demands of the healing wound. The final remodeling phase is characterized by the conversion of the relatively weak collagen from the previous phase into thick high strength collagen bundles.

The adequate supply of oxygen is of paramount importance in each phase of wound healing. During the inflammatory phase oxygen provides neutrophils with the critical ability to kill bacteria through superoxide generation. In the proliferative and remodeling phases oxygen is a key factor in collagen formation. Likewise oxygen provides for normal aerobic metabolism of the injured tissue.

The gastrointestinal tract, with the exception of the esophagus and lower rectum, is comprised of four layers: the outer serosa, the muscularis propria, the submucosa, and the mucosa. The submucosa consists of a layer of fibroelastic collagen matrix containing blood vessels and nerves. Halsted was the first to determine that the strength of the intestine is derived from the submucosal layer. It is the collagen fibrils within the submucosa that are mainly responsible for anastomotic integrity. Low collagen content is associated with reduced anastomotic bursting strength.

The etiology of anastomotic failures has been attributed to a variety of local and systemic factors. Local factors include tissue hypoperfusion, anastomotic tension, poor apposition of wound edges, radiation injury, and distal obstruction. The first three local factors contributing to failure are affected by surgical manipulation of tissues. Oxygen delivery to tissues is a function of the oxygen content of blood multiplied by the blood flow rate within a volume of tissue. Blood oxygen content (BOC) of whole blood is given by the following expression:

$$BOC = \text{Oxygen bound to hemoglobin} + \text{Dissolved Oxygen}$$

$$BOC = 1.34 * Hb * SO_2 + 0.003 * PO_2$$

Where, 1.34 (ml/g) is the amount of oxygen functionally carried by one gram of circulating hemoglobin, Hb (g/dl) is hemoglobin, $SO_2$ is percent hemoglobin oxygen saturation, 0.003 (ml/100 ml/mmHg) is the solubility of $O_2$ in plasma at 37° C., and $PO_2$ (mmHg) is the partial pressure of oxygen within the blood. Under normal physiologic conditions (Hb=15 g/dl, $SO_2$=0.98, and $PaO_2$=100 mmHg), BOC is 20 ml $O_2$/100 ml arterial blood.

As arterial blood flows through the capillary beds of the intestine, the blood cell hemoglobin desaturates as oxygen diffuses toward the supported tissue. The degree of desaturation from tissue oxygen extraction varies based on the flow of oxygenated blood through the tissue as well as the metabolic needs of the target tissue. Auto-regulation in the intestinal microcirculation allows for flow adjustment within limits responsive to demand. Under the normal flow conditions in canine ileum of 30-140 ml/min/100 g of tissue, oxygen extraction is flow-independent. The tissue is able to extract an adequate amount of oxygen to support aerobic cellular metabolism. Flow rates less than 30 ml/min/100 g oxygen extraction is flow-dependent and the tissues may not be able to support aerobic metabolism. Human small intestine has the same threshold for flow dependent oxygen. Hypovolemia and shock are contributing factors to anastomotic failure, where normovolemic anemia is tolerated if perfusion is adequate.

Surgical manipulations of anatomy during bowel resection as well as the creation of a surgical anastomosis cause a perturbation in tissue perfusion. A canine model demonstrated a reduction in mucosal blood flow at an end to end colonic anastomosis regardless of the technique employed. However, the absolute reduction is dependent on technique. Using a circular stapler, an anastomosis formed with a staple gap equal to the measured thickness of the interposed bowel walls yielded a 43 percent reduction in blood flow, whereas a staple gap of half the measured thickness yielded a 71 percent flow reduction. A single layer sutured anastomosis resulted in a 27 percent flow reduction while a 59 percent flow reduction was recorded in a two layered sutured anastomosis. Perianastomotic serosal measurements were taken intra-operatively on both the proximal and distal aspects of the anastomosis within 1 cm of the suture line. Altered perfusion at the rectal stump correlated with subsequent anastomotic leaks. Blood flow was measured by laser Doppler at the proximal side of an end-to-end colorectal anastomosis reveals a significant reduction in flow after requisite dissection. In summary, anastomotic failure occurs when perfusion fails to provide the inputs needed to support tissue healing.

One representative application of the present invention is in the performance of a bowel resection secondary to a bowel obstruction. Often a mechanical bowel obstruction is caused by an adhesion which causes the bowel to twist upon itself, or a hernia which incarcerates or strangulates the bowel. The blood supply to the bowel can be compromised leading to ischemia, or infarction. Intra-operatively, the surgeon qualitatively determines if the bowel is viable after it has been untwisted or freed. If the bowel does not appear viable the bowel is resected. Often qualitative methods are not accurate in determining bowel viability. If the bowel 'pinks up' then it may be salvageable. Questionable segments of bowel are either resected during the initial surgical procedure or left to 'declare themselves' over a number of hours resulting in the performance of a 'second look' operation to determine bowel viability. An advantage of the present invention is the ability to quantitatively assess bowel oxygenation at the time of surgery to ensure viability. If a segment is not viable and needs to be resected, the present invention can guide the surgeon in selection of a viable resection margin. The anastomosis is then performed on tissue in which normal perfusion has been confirmed.

One representative application of the present invention is in the creation and monitoring of tissue flaps. Cancer of various types, i.e. breast, skin, etc., often cause removal of significant volumes of tissue during an attempt at curative resection. Traumatic injury may result in severed limbs or avulsed portions of tissue. The resulting tissue loss is often replaced by native tissue transposed from other parts of the patient's body. Free tissue flaps are flaps that are completely removed from their native position along with the supplying vascular pedicle. The free flap vasculature is then reconnected to vessels near the tissue void. The vascular anastomosis may fail due to leakage, stricture, or occlusion from inappropriate clot formation. The present invention enables resolution of flap oxygenation in either a point or area fashion, both for the intra-operative confirmation of tissue perfusion, and post-operative monitoring. Current technology is limited to qualitative measures of blood flow. The present invention presents real time quantitative assessment of tissue oxygenation.

One representative application of the present invention is in the monitoring of patient oxygenation. A current method of continuously and non-invasively monitoring a patient's oxygenation is through the use of pulse oximetry. In pulse oximetry the patient's blood is interrogated with light to determine the percentage of blood that is saturated with oxygen. Unfortunately this technique is limited by technical and physiologic factors. Ambient light and motion affect the pulse oximeter's ability to render a suitable signal. Poor blood flow in critically ill patients can often render pulse oximetry useless as the pulsatile signal cannot be resolved. The present invention enables an accurate measure of tissue oxygenation independent of blood flow in a robust manner.

One representative application of the present invention is in the monitoring of a disease state of the brain. There are numerous conditions (trauma, stroke, procedures, cancer, infection, inflammation, etc) that can affect brain perfusion/oxygenation, whether through primary means such as vessel occlusion or hemorrhage; or through secondary means by alteration of intracranial pressure. Current technology fails to provide real time measurement of direct brain oxygenation/perfusion. The present invention provides for real time measurement of brain perfusion/oxygenation through trans-cranial, intra-cranial, or extra-cranial means. The device can be positioned on an infant, over the fontanel in order to interrogate underlying brain tissue. Alternatively the device can be placed intra-cranially through a trans-cranial port, or implanted in the brain tissue to allow for continuous monitoring over extended periods of time. The device can be positioned on the eye to interrogate the internal structures such as the optic nerve, or retina.

One representative application of the present invention is in the monitoring of organs. In this application the device can be temporarily placed or permanently implanted into or on the surface of an organ. Alternatively the device can be ingestible to monitor the gastrointestinal tract. An ingestible device could map the oxygenation, and/or other physiological parameters of the GI tract.

The present invention includes a surgical instrument, probes, and methods for assessment of phosphorescent or fluorescent lifetime of an injectable probe or natural auto fluorescence. In one configuration, at least one sensor is configured to obtain biological tissue oxygenation utilizing the technique of oxygen dependent quenching of phosphorescence of an injectable probe. In another embodiment, the present invention measures lifetime of a marker or other probe in or on the body. In a further embodiment, lifetime of phosphorescence or fluorescence produced from native biologic tissue is assessed.

Other potential applications include but are not limited to the monitoring/recording of a transplanted organ or appendage, intra-cranial, intra-thecal, intra-ocular, intra-otic, intra-nasal, intra-sinusoidal, intra-pharyngeal, intra-laryngeal, intra-esophageal, intra-tracheal, intra-thoracic, intra-bronchial, intra-pericardial, intra-cardiac, intra-vascular, intra-abdominal, intra-gastric, intra-cholecystic, intra-enteric, intra-colonic, intra-rectal, intra-cystic, intra-ureteral, intra-uterine, intra-vaginal, intra-scrotal; intra-cerebral, intra-pulmonic, intra-hepatic, intra-pancreatic, intra-renal, intra-adrenal, intra-lienal, intra-ovarian, intra-testicular, intra-penal, intra-muscular, intra-osseous, and intra-dermal physiologic/biomechanical parameters.

The present invention relates to medical devices capable of measuring physiologic and mechanical properties of tissue. One embodiment of the invention relates to coupling sensing elements with a surgical instrument to determine tissue viability during surgery by measuring the optical time response from a light re-emitting medium. In a specific embodiment, an oxygen-sensitive phosphorescent oxygen sensing probe is injected into tissue, and a laparoscopic interrogator uses optical sensing elements to determine tissue oxygenation based on the optical response (i.e. lifetime) of light emitted by the phosphorescent probe.

The sensing elements associated with the invention may sense mechanical or biological properties. The sensing instruments may include one or more sensing modalities. The sensing modalities may include mechanical, optical, chemical, electrical, or other means for generating a signal indicative of a property of a subject tissue. In one embodiment, the sensing elements measure oxygenation through the use of a medium containing a phosphorescent probe or phosphor delivered into tissue. Other embodiments measure oxygenation through oximetry-based techniques. Further embodiments measure perfusion or flow rates through the time response of a fluorescent or phosphorescent medium introduced into the tissue.

In an embodiment, the sensing elements are incorporated into, or coupled to, the working surface (i.e. tissue contacting surface) of a surgical instrument for manipulating biological tissue. Instruments may include traditional open, laparoscopic, endoscopic, bronchoscopic, otoscopic, opthalmoscopic, laryngoscopic, cystoscopic, colposcopic, intravascular, intraluminal, robotic, or other minimally invasive tools such as a purpose-built tissue interrogator or instrumented standard instrument such as a grasper, needle driver, stapler, clip applier, catheter, scissor, cautery, or retractor. Instruments may also include interrogators or other devices that may or may not be minimally invasive and may interrogate the internal and/or the external surface of tissue.

The sensing elements may include mechanical and optical sensing modalities. Mechanical sensing includes, but is not limited to, pressure sensors that monitor tissue interaction forces including compression pressure and tissue tension. Optical sensing elements include but are not limited to light emitters including light emitting diodes (LEDs), broad band light sources, and laser diodes (LDs), and light receivers including photodiodes (PDs) and silicon photomultipliers (SiPMs), CCD arrays, CMOS imaging sensors, cameras, and spectrometers. The sensors may make measurements at a single discrete location or at a plethora of locations. The optical sensing elements are configured to measure at least one of tissue oxygenation, oxygen delivery, oxygen utilization, tissue characterization, and tissue general health using oximetry, phosphorescent techniques, or spectroscopic techniques, and at least one of tissue perfusion, tissue flow dynamics, tissue oxygen content, tissue chemical composition, tissue immunologic activity, tissue pathogen concentration, or tissue water content using fluorescence or phosphorescence based techniques. The fluorescence and phosphorescence based techniques include but are not limited to the following: monitoring and analyzing the intensity and time course of a fluorescent or phosphorescent response responsive to the injection or activation of a fluorescent or phosphorescent medium (e.g., fluorescein or indocyanine green injection), determining oxygen quantities by measuring oxygen-dependent quenching of fluorescent or phosphorescent radiation using a sensitive material (e.g., ruthenium) by both intensity and time-resolved methods, determining oxygen concentration based on the quenching time response (lifetime) of injectable oxygen sensitive phosphorescent probes (e.g., oxygen-dependent quenching phosphorescent nano sensors), and determining the target tissue property by quantitative fluorescent or phosphorescent methods (including the use of quantum dots, or other biomarkers incorporating light re-emitting properties). In one configuration the device senses perfusion using flourescein, or IC green, or other imaging agent. In one other configuration the device senses native oxygen quenching or phosphorescence.

Measurement of tissue oxygenation or other tissue characteristics can be measured in a gated fashion to standardize the measurement and allow for comparison. One representative example of said gated measurement is the measurement of tissue oxygenation at a known interaction force(s) such as compression pressure. Measurements may also be gated to physiologic parameters such as respiration and cardiac output.

PCT Patent Application No. PCT/US2006/013985, which is hereby incorporated herein by reference in its entirety, describes a system and methodology for using the information gathered by surgical instruments having sensors in an adaptive, patient-specific manner. The present invention can be used to predict outcome, the likelihood of success or of failure, or guide surgical procedure, and as described in PCT/

US2006/013985, US Patent Application Publication No. 2012/0116185, which is hereby incorporated herein by reference in its entirety, and U.S. Pat. No. 8,118,206, which is hereby incorporated herein by reference in its entirety. Furthermore the present invention can be configured as an adjunct sensing system, and as described in US Patent Application Publication No. 2012/0116185 and U.S. Pat. No. 8,118,206. Additionally, the present invention can be powered by radiofrequency techniques, and as described in US Patent Application Publication No. 2010/0081895, which is hereby incorporated herein by reference in its entirety.

Tissue parameters can be measured by a variety of methods. One technique utilized by the present invention measures tissue oxygenation levels via utilizing oxygen dependent quenching of phosphorescence via a systemic or locally injected phosphorescent oxygen sensing molecular probe for oxygen measurements. See, for example, U.S. Pat. No. 4,947,850, which is hereby incorporated herein by reference in its entirety, U.S. Pat. No. 5,837,865, which is hereby incorporated herein by reference in its entirety, U.S. Pat. No. 6,362,175, which is hereby incorporated herein by reference in its entirety, U.S. Pat. No. 6,165,741, which is hereby incorporated herein by reference in its entirety, U.S. Pat. No. 6,274,086, which is hereby incorporated herein by reference in its entirety, U.S. Pat. No. 7,575,890, which is hereby incorporated herein by reference in its entirety, and US Patent Application Publication No. 2013/0224874, which is hereby incorporated herein by reference in its entirety. The phosphorescent oxygen sensing probe can include a phosphorescent metalloporphyrin core encapsulated inside hydrophobic dendrimers, which form a protecting shell that isolates the chromophore from direct contact with the environment, controls oxygen diffusion, and enables control over the probe's dynamic range and sensitivity. The metalloporphyrin core can be constructed with different elements. Palladium (Pd) and platinum (Pt) are two elements that can be utilized. The advantage of a platinum based core over a palladium based core is its quantum efficiency. The increase in the quantum efficiency of the phosphor allows for a significant increase of light output when compared to the Pd based molecule; more light returned per molecule allows for the use of fewer molecules to achieve the same signal returned to the device. Alternatively injection of the same amount of molecule enables the use of less sensitive (less expensive) photo-detectors. Peripheral PEGylation of the dendritic branches ensures high aqueous solubility of the probe whilst preventing interactions with biological macromolecules. The overall size of the molecular probe affects the probe's ability to be cleared by the kidney. Faster clearance limits the agent's exposure to the patient. The size can be varied through the modification of the dendrimer length, number of dendrimers, and the extent of PEGylation.

In one embodiment of the probe, the core, Pd-meso-tetra-(3,5-dicarboxyphenyl)tetrabenzoporphyrin (PdTBP), is encapsulated by eight generation 2 poly-arylglycine (AG2) dendrons; each of which are PEGylated with monomethoxy-polyethyleneglycol amine (PEG-NH2) groups (Av. MW 1,000 Da), having on average 21-22 monomeric —(CH2CH2O)— units. The molecular weight of the probe dendrimer was found to be in the range of ~26,000-44,000 Da with a maxima of 35,354 Da as determined by MALDI mass spectroscopy. The phosphorescence quenching method relies on the ability of molecular oxygen (O2) to quench phosphorescence of excited triplet state molecules in the environment. In biological systems phosphorescence quenching by oxygen occurs in a diffusion controlled fashion and is highly specific to O2, since O2 is the only small-molecule dynamic quencher present in sufficiently high concentrations. The dependence of the phosphorescence lifetime ($\tau$) on the partial pressure of oxygen (pO2) through the range of biological concentrations is well described by the Stern-Volmer equation: $1/\tau = 1/\tau 0 + kq \times pO2$, where $\tau$ is the phosphorescence lifetime at a specified oxygen pressure pO2, $\tau 0$ is the phosphorescence lifetime in the absence of oxygen (pO2=0), and kq is the quenching constant. One molecular oxygen probe has a quenching constant, kq, of approximately 326 mmHg$^{-1}$s$^{-1}$, and a $\tau 0$ of 210 μs over the range of physiologic pH, 6.2-7.8, and constant temperature of 36.5° C. The calibration parameters of said probe, kq and $\tau 0$, change linearly with respect to temperature. The quenching constant, kq, increases from 211 mm Hg$^{-1}$s$^{-1}$ to 338 mmHg$^{-1}$ s$^{-1}$ with the rise of temperature from 22° C. to 38° C., which corresponds to the temperature coefficient of 7.8 mm Hg$^{-1}$s$^{-1}$/° C. The absorption spectrum of said probe has maxima at approximately 448 nm and 637 nm with a phosphorescence emission maximum of 813 nm. Excitation at multiple wavelengths (either separately or simultaneously) confers an application specific advantage of being able to interrogate and distinguish tissue properties at differing penetration depths or layers. A combination of multiple pO2 values in a field of view (e.g., where different tissue layers are differently oxygenated) will manifest itself as a combination of lifetimes (a sum of exponential decays); multiple pO2 values and corresponding concentrations can be determined through means described herein.

FIG. 1a shows a representative system with sensing capabilities according to an embodiment of the present invention. This embodiment specifically depicts a surgical instrument 101, wherein the instrument is a minimally invasive device for manipulating biological tissue. The instrument may be designed for open, laparoscopic, endoscopic, or other surgical approaches as previously noted. The instrument interacts with tissue of body 103. In one embodiment, said tissue is intestinal tissue 107. One configuration of instrument 101 incorporates jaws 109 and 111 to interact with tissue 107. In one embodiment, one or more jaws 109 and 111 contain sensors or sensing elements 110 and 112 for measuring biological or mechanical properties of tissue 107. In a further embodiment, the jaws are configured to ensure constant compression pressure of tissue 107 against sensing elements in jaws 109 and/or 111. One or more jaws may contain an inflatable cavity, bladder, balloon, catheter, compression plate, or pressure sensor 113 for compressing tissue against one or more sensing elements. Jaws 109 and 111 may incorporate control electronics and sensing elements. Jaws 109 and 111 are coupled to instrument 101 and may either be a fixed distance apart, be able to move in a parallel motion, or move in a hinged motion. In one embodiment, the distal tissue contacting end of the instrument 101 is articulated at a joint 114 with one or more degrees of freedom.

In one embodiment, jaws 109 and/or 111 contain an applicator capable of delivering a medium into tissue 107. The medium may incorporate a fluorescent or phosphorescent oxygen sensing molecular probe. In one embodiment, the applicator comprises one or more microneedles incorporated into one of jaws 109 and 111. Said microneedles may take the form of a molded needle array. In another embodiment, one of more of jaws 109 and 111 incorporates needles with a porous surface for delivering the medium into tissue 107. In another embodiment the needles have at least one side hole, and an occluded tip. One embodiment of the present invention incorporates an integrated injection system. The injection system includes a vessel 117 that contains the medium 118. The medium 118 that has been introduced into tissue 107 is identified as 119. In one embodiment, the vessel 117 contains a number of metered doses of a medium 118 comprising the phosphorescent oxygen sensing molecular probe. Vessel 117 is coupled with the one or more needles associated with jaws 109 and/or 111.

In one embodiment, instrument 101 contains a handle or other component 121 that encloses one or more of control electronics, battery power sources, user interfaces, displays, and a wired or wireless communications interface. The instrument 101 or component 121 may include controls for adjusting compression pressure between jaws 109 and 111, articulating joint 113, administering injections from vessel 117, and operating sensing elements located in jaws 109 and/or 111. Component 121 may be optionally detachable from instrument 101, allowing for a partially disposable configuration of 101, in which 121 is reusable. The control electronics in 121 or other location on instrument 101 may communicate with an external interface 125 through a wireless or wired connection 123. The external interface may take the form of a free standing base station, a computer, a tablet style computing device or other portable electronic device with a display, or other device. External interface 125 may additionally be connected to an external network. Device 125 displays information to the clinician on display 127. This information may include tissue oxygenation, blood flow, maps of tissue oxygenation, compression pressure, warning information, predictions about the likelihood of success of the procedure, or other physiologic, mechanical, patient status, or situational information. Sensory substitution including audio, visual, vibration, or other techniques may be provided by instrument 101 or external device 125.

Figure 1B:
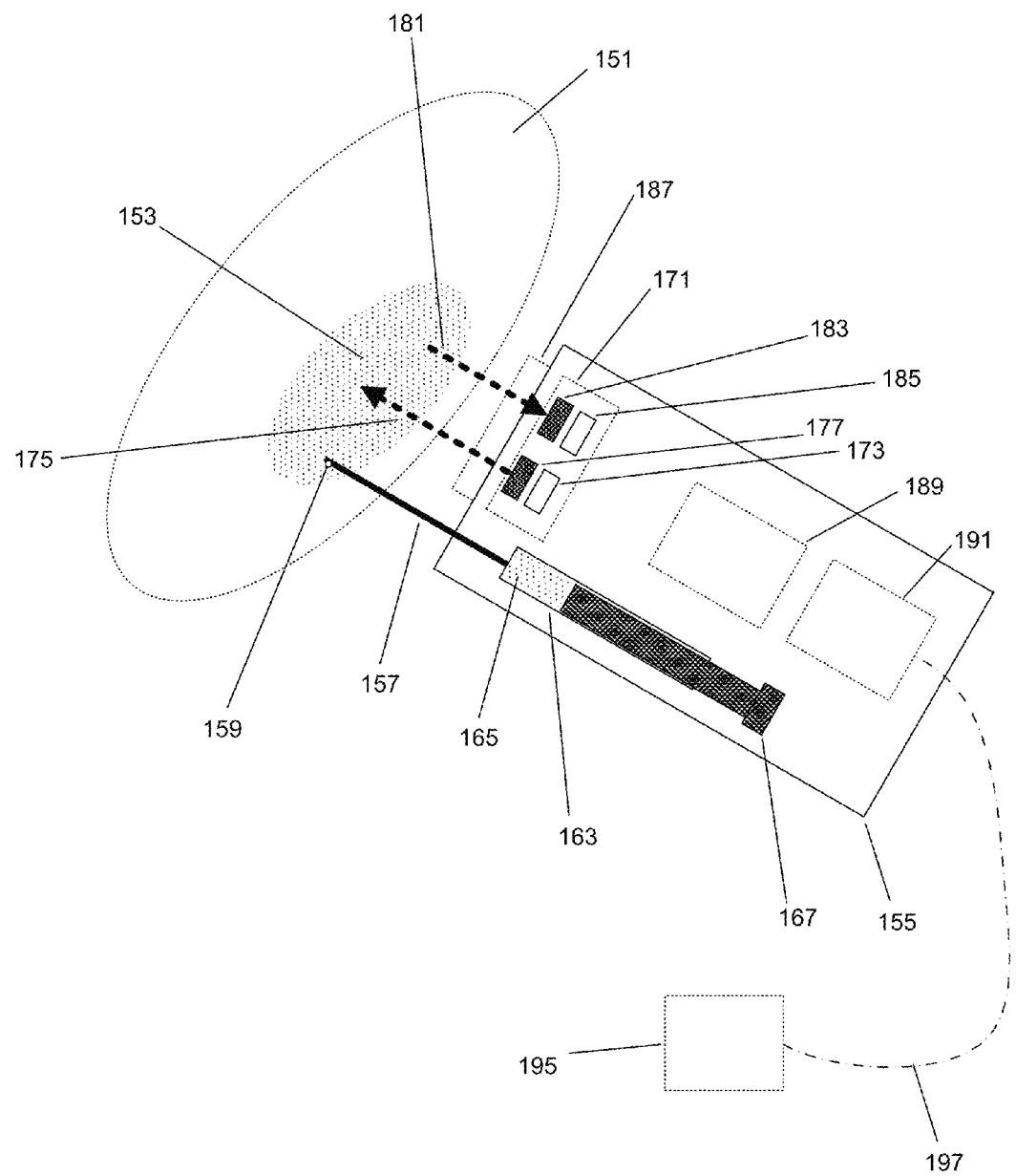
FIG. 1b shows a generic embodiment of a medical device with features.

FIG. 1b shows further detail of a representative medical device with sensing capabilities according to an embodiment of the present invention. A biological tissue 151 contains a medium 153. In one embodiment of the invention, medium 153 contains a phosphorescent oxygen sensing molecular probe injected into tissue 151. The medium may be introduced systemically or may be injected locally. In one embodiment, one or more needles or delivery cannulas 157 with at least one orifice 159 are used to locally inject medium 153. A medical device 155 is configured to interrogate tissue 151. Device 155 may also comprise an applicator for delivery of a medium. In one configuration, needle 157 is a microneedle and orifice 159 is one or more holes on the lateral side of said needle. A vessel or syringe 163 contains medium 165; medium 165 is the same material as medium 153 prior to injection into tissue 151. An injector 167 may be used to inject medium 165 into tissue 151 as represented by medium 153 in the tissue. Injector 167 may be manually controlled or may be motorized or otherwise actuated. Injector 167 may be configured to provide metered doses of medium 165. Vessel 163 and injector 167 may be an integral part of medical device 155, may be an accessory to medical device 155, or may be configured as an independent injection system. Medical device 155 contains at least one sensor 171, which further contains sensing elements 173 and 185. In one embodiment, sensing element 173 is a light emitter source that emits light 175 that optionally passes through an optical filter 177 into the medium 153 of tissue 151. Upon incident light 175, medium 153 re-emits an optical response light 181. Optical response 181 optionally passes through an optical filter 183 to an optical detector 185. A further sensor 187 may provide a measurement of contact or of pressure between a surface of instrument 155 and tissue 151. Components of sensor 171 are coupled with processor 189 that controls light source 173 and acquires signals from detector 185. Processor 189 controls light emission from 173 and processes signals from 185 so as to perform a sensing operation. In one embodiment, a communication interface 191 communicates with an external base station or other device 195 through a link 197. Link 197 may be a wireless communication between device 155 and base station or display 195.

In one embodiment of the present invention, medium 153 and 165 contains fluorescent or phosphorescent oxygen sensing molecular probe. Light source 173 may be a narrow band light source such as an LED or laser, or may be a broadband source such as a white light source. The peak emission wavelength of the narrowband source is selected to be at or near an absorption peak of the probe (e.g., an excitation wavelength of the probe) in medium 153. Filter 177 may be used to further restrict incident light 175 to wavelengths in or near the absorption wavelength region of the probe. The probe re-emits light 181 which then optionally passes through filter 183 to isolate the emission light 181 from the incident light 175. Light detector 185 senses the intensity of received light 181. In one configuration, detector 185 is a single point detector such as a PD, APD, SiPM, or similar device. In an alternate configuration, detector 185 is a multi-point detector such as a camera or an array of single point detectors. The camera may be CCD, CMOS, or other technology and may be directly at the tissue contacting surface of instrument 155 or optically coupled at a remote location. The array of single point detectors may be PD array, SiPM array, linear CCD or other technology. In one configuration, processor 189 commands light pulses from source 173 and analyzes the time response of the signal received by detector 185 using time domain signal processing techniques. In an alternate configuration, processor 189 commands modulated light such as a sinusoidal intensity profile from source 173 and analyzes the measured signal from detector 185 to determine the phase lag through frequency domain signal processing techniques. In one configuration the probe in medium 153 quenches the lifetime of the phosphorescent re-emission in response to oxygen in the vicinity of the probe. This relationship between oxygenation and phosphorescent lifetime may follow the Stern-Volmer relationship. Time domain or frequency domain techniques may be used by the signal processor 189 to quantitatively resolve the corresponding oxygen content or concentration in a location of tissue 151. By resolve it is meant to calculate, compute, determine, assess, or acquire the solution for oxygen content or concentration in the target tissue. An exemplary implementation of said time domain or frequency domain techniques is taught in U.S. Pat. No. 6,707,168-B1. Oxygen content may be represented as a number or shown as a map of oxygenation on either device 155 or an external display unit 195. The oxygen content may be used to predict the likelihood of success or failure of the surgical procedure, or guide a surgical procedure. An exemplary implementation of predictive or guidance techniques is taught in US 2009/0054908 A1, which is hereby incorporated herein by reference in its entirety. In one embodiment, instrument 155 is a minimally invasive surgical instrument. In another embodiment, device 155 is an anvil of a surgical stapler. In another embodiment, device 155 is an adjunct to a surgical instrument, such as an accessory to a surgical stapler anvil. In another embodiment, device 155 is an internally implantable sensor. And in another embodiment, medical device 155 is an externally wearable device such as a patch or is an implantable sensor.

In one configuration of the present invention, the medical device (such as a surgical instrument) 101 or 155 or other embodiments are configured to sense oxygenation in multi-layered tissue, or to discriminate oxygenation at different depths of tissue. Using a phosphorescent oxygen sensing probe having multiple absorption wavelengths in medium 119 or 153, the instrument 101 or 155 can irradiate and excite a subset of the probe injected into tissue 107 or 151 based on the excitation wavelength emitted from device 101 or 155 since the penetration depth in tissue is wavelength-dependent. Oxygenation can be discriminated at two or more depths or layers by exciting the tissue sequentially with multiple excitation wavelengths at or near absorption peaks of the probe, and determining the corresponding quenching response. Sensing the deeper values will be a summation of multiple layers, oxygenation at deeper layers can be determined by accounting for the sensed oxygen at shallower layers. In an alternative approach, the phosphorescent decay of various oxygenation levels in heterogeneous luminescence systems (i.e. mixed oxygenations within the tissue sample) can be determined through deconvolution methods to produce a spectrum of oxygenation.

In one embodiment of a sensing medical device, a plethora of sinusoidally modulated excitation light outputs are generated (either simultaneously, separately, or combined into a time varying frequency signal such as a chirp) and frequency domain techniques are utilized to determine the spectrum of phase lag of the received signal from an injected phosphorescent medium. By determining the relative contributions of each phase lag, a quantitative spectrum of tissue oxygenation may be generated. In another embodiment, time domain techniques are utilized to determine the time response of the medium to a pulse of light. Multiple exponential fitting of the decay can be used to generate a quantitative spectrum of tissue oxygenation.

Figure 2:
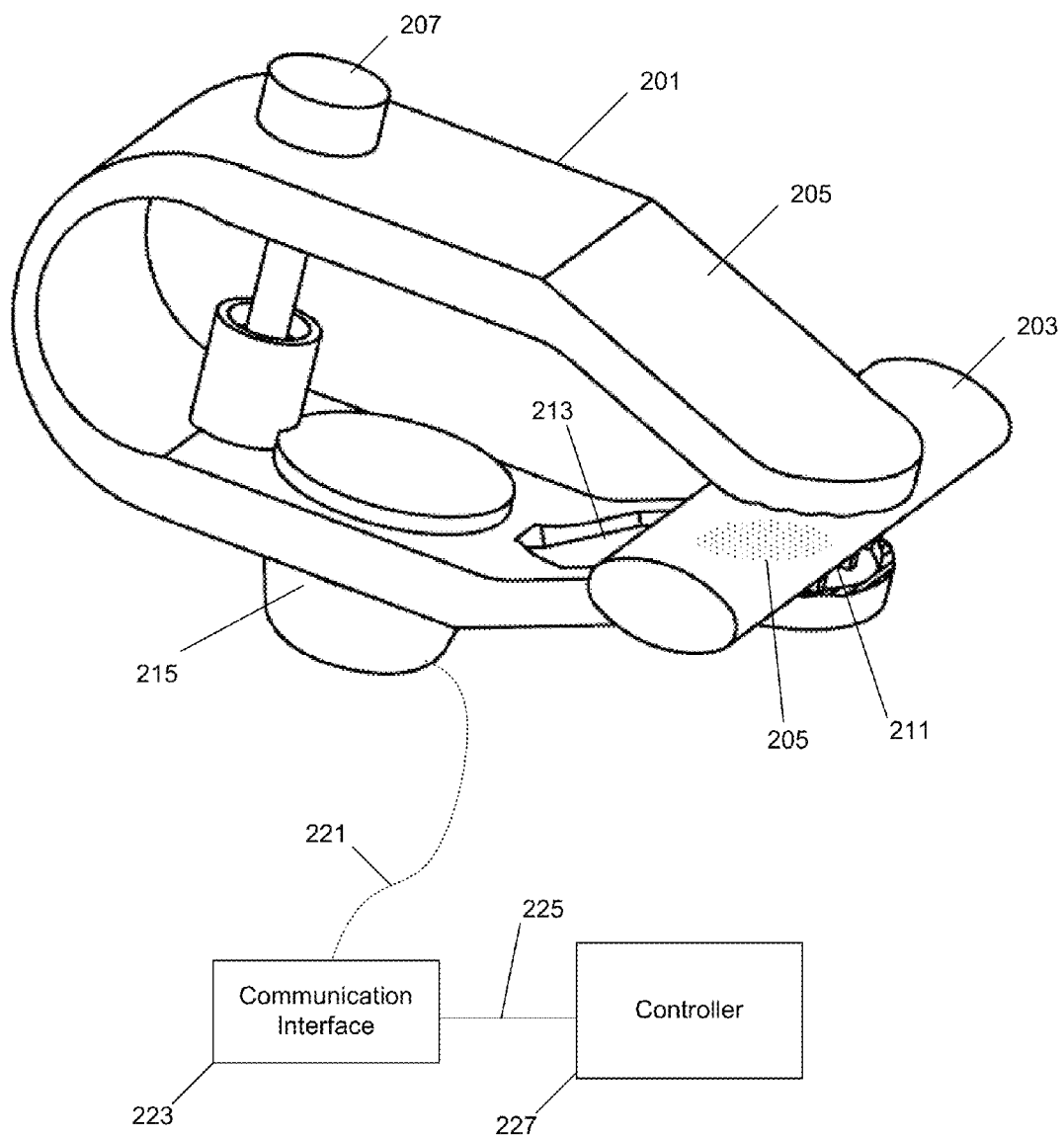
FIG. 2 shows a representative embodiment of a surgical instrument taking the form of an interrogator with sensing capabilities.

FIG. 2 shows a tissue interrogator. The interrogator 201 evaluates properties of tissue 203. In one embodiment, jaws 205 grasp tissue 203. A compression control device such as screw 207 or a compression device (e.g., a balloon or compression plate) affixed to jaws 205 regulate pressure on tissue 203. Sensing elements 211 are integrated into the one or more tissue contacting surfaces. In one embodiment, an injection system is incorporated into a cavity 213 of the device. Needles in cavity 213 are used to deliver a medium 205 into tissue 203. In one embodiment, a phosphorescent oxygen sensing probe 205 is injected into tissue 203. Sensing elements 211 obtain data to measure tissue oxygenation by illuminating tissue with a light source and assessing the time response of the re-emitted light (i.e. phosphorescent quenching time response). Control electronics 215 operate the sensing elements 211 and are communicatively coupled through 221 to communication interface 223. Interface 223 is coupled through 225 to an external controller or user interface 227.

Figure 3:
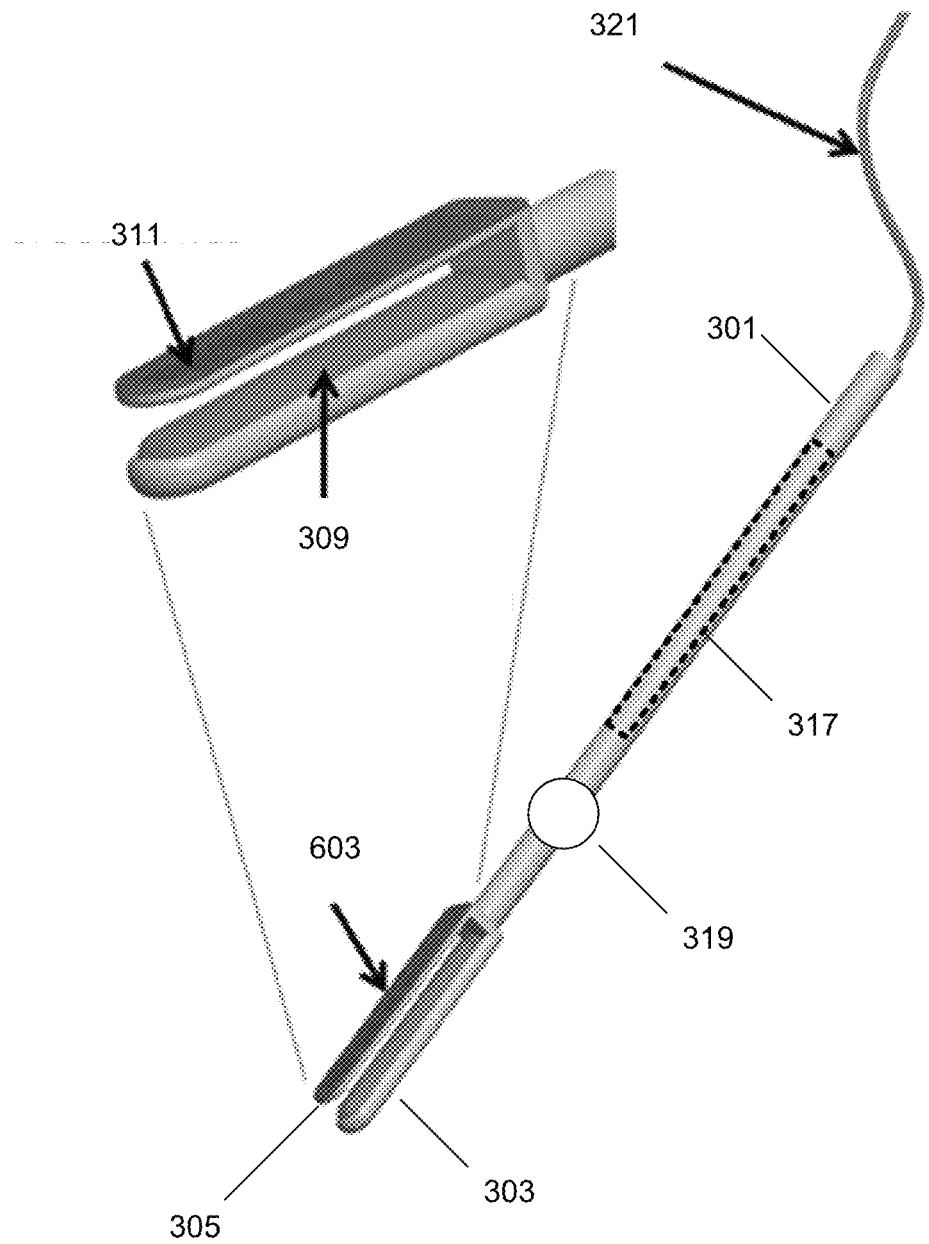
FIG. 3 shows a representative embodiment of a minimally invasive surgical instrument taking the form of an interrogator with sensing capabilities.

FIG. 3 shows one embodiment of a wand-type tissue interrogator designed for minimally invasive surgical interventions. Wand 301 contains lower jaw 303 and upper jaw 305 to interact with (i.e. enclose) a biological tissue. Lower jaw 303 contains a compression device 309 to standardize and maintain consistent compression pressure of the tissue. Upper jaw 305 contains control electronics 311 and sensing elements on the tissue contacting surface. In one embodiment, jaws 303 and/or 305 contain an injection system for introducing a medium into the tissue. This medium may include a phosphorescent oxygen sensing probe or another agent capable of imaging, diagnostic, or therapeutic purposes. The applicator injection system 317 may be incorporated into the handle or body of instrument 301. This may include a vessel containing one or more doses of the medium. A user can administer the dose precisely from the instrument 301 to needles in jaws 303 and/or 305. The needle may be microneedles that may further take the form of a micromolded needle array. They may also take the form of porous needles that saturate the tissue in the region for microinjection of the medium into the tissue in contact with the instrument jaws. Jaws 305 and 303 may be fixed relative to each other, or able to open and close. The distal end of the instrument may be articulated at joint 319. In one embodiment, instrument 301 fits through a standard laparoscopic surgical instrument port and articulates at joint 319 to position jaws 303 and 305 around a tissue. In one configuration, a tube 321 is used to inflate or otherwise control compression device 309. In a further configuration, compression device 309 is a balloon catheter. In another embodiment, a tube 321 is used to deliver the medium for injection into the tissue. In a further embodiment, the sensing instrument is connected via a wired or wireless connection to an external interface. In one configuration, the instrument interacts with intestinal or colonic tissue and measures tissue oxygenation at or near the site of a surgical anastomosis. The instrument may take measurements before, during, and after the anastomosis is created. It may be used as a stand-alone device or in combination with an additional sensing instrument such as a sensing anvil for a surgical stapler. This configuration or another embodiment of an interrogator may be used to take measurements on the internal and/or external surface of tissue. It may take measurements at a single location or at a plethora of locations.

Figure 4A:
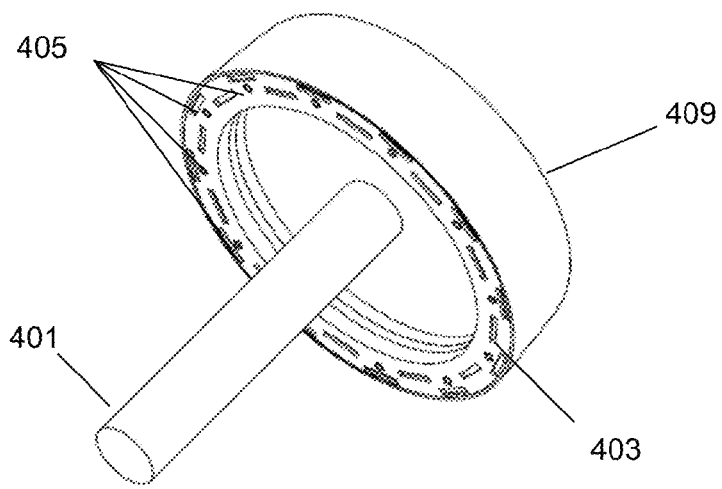
FIG. 4a shows a representative embodiment of a surgical instrument taking the form of surgical stapler anvil with sensing capabilities.
Figure 4B:
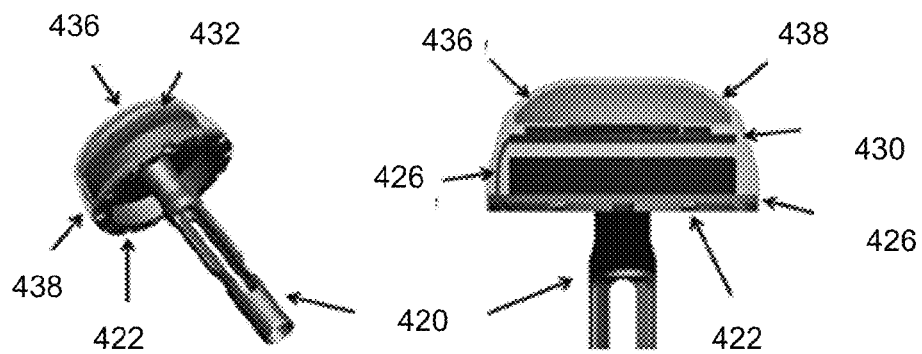
FIGS. 4b and 4c show another representative embodiment of a surgical instrument taking the form of surgical stapler anvil with sensing capabilities integrated into the staple form.
Figure 4C:
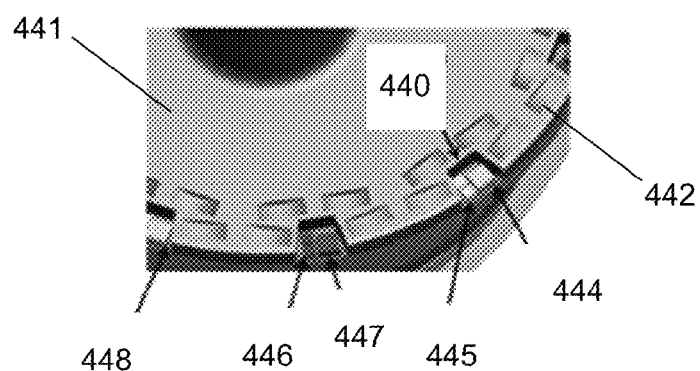

FIG. 4a shows a representative embodiment of an anvil 401 for a surgical stapler instrument with sensing capabilities. Working surface 403 makes contact with the biological tissue. Sensing elements 405 make contact with tissue at working surface 403. The sensing elements may be an integral part of anvil 401 or an accessory. In one configuration, the sensing elements are integrated into an accessory 409 that couples to the anvil. The present invention includes sensing elements both directly integrated into and also otherwise associated with the surgical instrument (i.e. an accessory or adjunct device). FIG. 4b shows one representative configuration of the present invention with sensing elements incorporated into cutouts 422 in the face of working surface of a modified surgical stapler anvil 420. In one embodiment, anvil 420 contains a sensor element interface circuit 426 couples via a flexible cable to a control circuit 430. Control circuit 430 may contain a processor for controlling and interpreting sensor elements. The control circuit may communicate via a wireless transceiver 432. The device is powered via a battery 436. All components are contained within a shell, cap or cover 438. FIG. 4c further details one embodiment where optical 446 and mechanical sensing elements are integrated into the cavities in face 441 of the anvil between staple forms 442. 444 represents a mechanical sensor such as a pressure transducer die that measures compression pressure on surface 442 of the anvil. 445 represents an integrated temperature sensor. 446 and 447 represent optical sensor elements, where 446 are one or more light emitters and 447 is a photodetector. In one embodiment the optical sensor elements include multiple light emitters at more than one peak wavelength so as to enable depth-resolved sensing. Sensor elements 444-447 may be located in the cavities in various configurations including combined together or distributed across the surface 441. A cover lip 448 encloses the edge of the sensor elements. In one embodiment, the sensing components are incorporated into a shell that couples to a surgical stapler anvil, or alternatively to the stapler body or other component. In another embodiment, the sensing components are incorporated directly into an anvil for a surgical stapler and replace a traditional non-sensing anvil. In both cases, the sensing shell or replacement anvil serve as an accessory or adjunct to the surgical stapler and may be optionally coupled to the stapler.

The sensing anvil may be used as a stand-alone device or in combination with an additional instrument such as an interrogator.

Figure 4D:
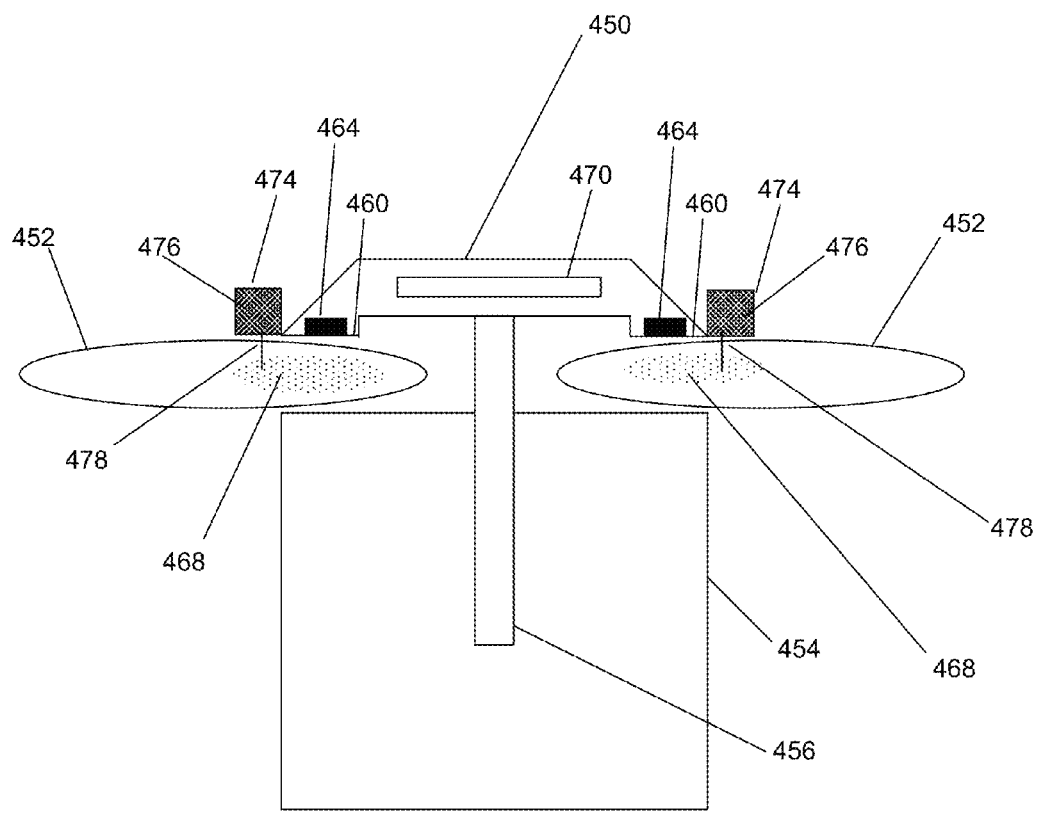
FIG. 4d shows a generic embodiment of a surgical instrument taking the form of surgical stapler anvil with sensing capabilities.

FIG. 4d shows a representative embodiment of a surgical stapler anvil 450 with sensing capabilities according to the present invention. Anvil 450 contacts tissue 452 and compresses tissue 452 against a surgical stapler housing 454. Anvil 450 is coupled to housing 454 via a stalk 456. Surgical staple forms are integrated into working surface 460 of the surgical stapler anvil 460. In one embodiment of the invention, one or more sensors or sensor elements 464 are incorporated into cavities formed in the working surface 460 between staple forms. In one embodiment, sensors or sensor elements 464 are configured to measure oxygenation of tissue 452 by interrogating a probe in medium 468 which has been injected into said tissue. In one embodiment, medium 468 contains a phosphorescent probe whose lifetime is indicative of oxygen content and sensor elements 464 comprise light emitters and detectors. Sensors or sensor elements 464 may also comprise pressure sensors for detecting contact or compression pressure on tissue 452. Sensors or sensor elements 464 may also comprise temperature sensors and/or pH sensors. Sensors or sensor elements 464 are coupled to a processor or signal processor 470. In one embodiment, processor 470 controls one or more light emitters, receives signal from one or more light detectors, and determines oxygenation responsive to said signals. Processor 470 may also utilize pressure sensor data for gating a reading to a predefined pressure to ensure consistent readings. Processor 470 may also utilize temperature and/or pH sensor data for calibrating the oxygenation measurement. In one embodiment, an applicator 474 is coupled with anvil 450. Applicator 450 may contain a medium 476 or be coupled to a syringe or other vessel containing the medium. Applicator 474 may contain one or more needles or a microneedle array 478 to inject the medium into the tissue 452 as represented by 468. Applicator 474 may be a standalone device or integral to anvil 450. Applicator 474 may be keyed to anvil 450 so as to delivery a microinjection at the location of sensor elements 464.

In one embodiment of the present invention, the surgical instrument contains LEDs, lasers, or other light sources on the working surface of the surgical instrument that introduce excitation light into a phosphorescent or fluorescent medium delivered into a tissue in contact with said surface. Re-emitted light (i.e. fluorescent or phosphorescent emission) is sensed by PDs, avalanche photodiodes (APDs), photo-multiplier tubes (PMTs), SiPMs, or other photodetectors. Control electronics measure the time response of the oxygen-dependent quenching of the phosphorescent response and said information is used to determine tissue oxygenation. Time domain or frequency domain based techniques may be used to determine tissue oxygenation. In one embodiment, the medium incorporating phosphorescent oxygen sensing probes may be introduced using an injector integral to the surgical instrument. Microneedle, needle arrays, surface absorption, or other approaches may be used to introduce the medium. An injection system may be incorporated into the surgical instrument. In another configuration, a separate injection system is utilized which may be by traditional means (i.e. needle and syringe) or a stand-alone injector specifically designed to operate with the instrument. In one configuration, a stand-alone injector is keyed to the sensing anvil to align injection locations with sensor locations. These techniques may be applied to a laparoscopic interrogator, a stapler, a laparoscopic or other minimally invasive instrument, a robotic instrument, or an instrument for open surgery.

Figure 5:
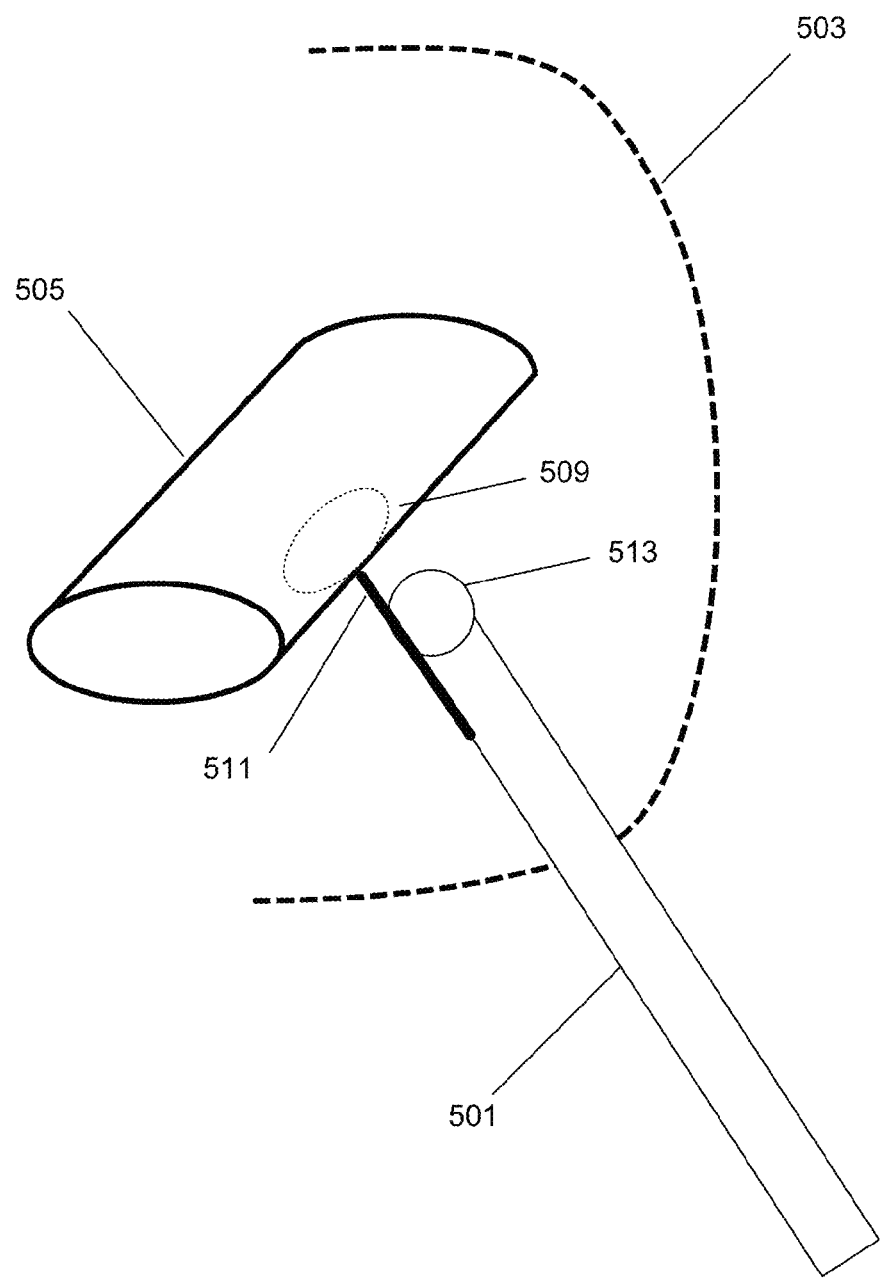
FIG. 5 shows a representative embodiment of an oxygen mapping system taking the form of a minimally invasive instrument with integrated applicator.

FIG. 5 shows an oxygen imaging system for minimally invasive surgery. Instrument 501 enters body 503 through a standard port of laparoscopic or endoscopic surgery or an existing lumen of the body. The instrument interrogates tissue 505. Tissue 505 has a region 509 where a medium containing a fluorescent or phosphorescent oxygen sensing probe has been introduced. In one embodiment, an injector 511 is incorporated into or coupled into the instrument 501. In an alternative embodiment, other methods of local injection or systemic bolus injection may be used. Instrument 501 incorporates an imaging system 513 at the distal end. The imaging system 513 illuminates the probe in region 509 and detects the oxygen-dependent quenching of the phosphorescent response. In one embodiment, imaging system 513 incorporates a camera and the system provides a 2D map of tissue oxygenation. The imaging system 513 may take on multiple embodiments which may comprise a standard camera (such as CCD or CMOS), an intensified camera system, linear array, or scanning sensor. Imaging system tip 513 may directly contain the camera, or it may be fiber optically coupled to a remote camera system. The map may appear as a quantitative image of tissue oxygenation, and may be further visualized in combination with traditional endoscopic video images. In a further embodiment, a 3D map conforming to the tissue shape is generated. The 3D map may be generated by registering multiple images from a single camera (such as using shape from motion techniques) or from multiple cameras (such as a stereo camera). One embodiment of the invention is a miniature sensing instrument 501 for assessing oxygenation inside of the eye. The instrument may measure oxygenation at a single location or by generating a 2D or 3D quantitative map of oxygenation. To minimize the tip of the miniature sensing instrument, optical fibers or other light guides couple the imaging system tip 513 to a remote detector. The system can detect and map areas of high and/or low oxygen or blood flow.

Figures 6A, 6B:
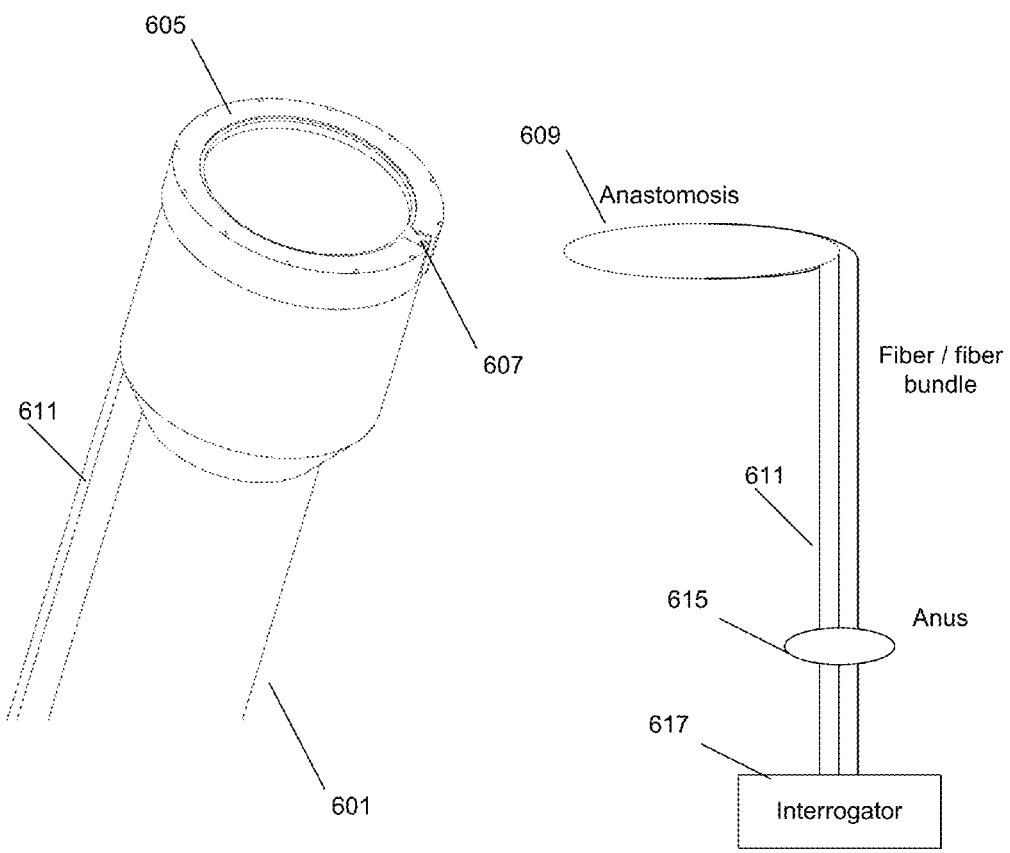
FIGS. 6a and 6b show a representative embodiment of an implantable sensing device.

FIG. 6 shows a configuration where a circular surgical stapler delivers a sensing device 605 on its working surface 607. The sensing device places a plethora of optical fibers around an anastomosis 609. Fiber bundle 611 passes through the anus 615 to interrogator 617. In one embodiment, the interrogator is configured to assess the phosphorescent lifetime of oxygen-dependent quenching of an injectable oxygen sensing probe. In a further embodiment, the sensing device 605 is bioabsorbable and the optical fibers can be readily removed at a time after the surgical procedure.

Figure 7:
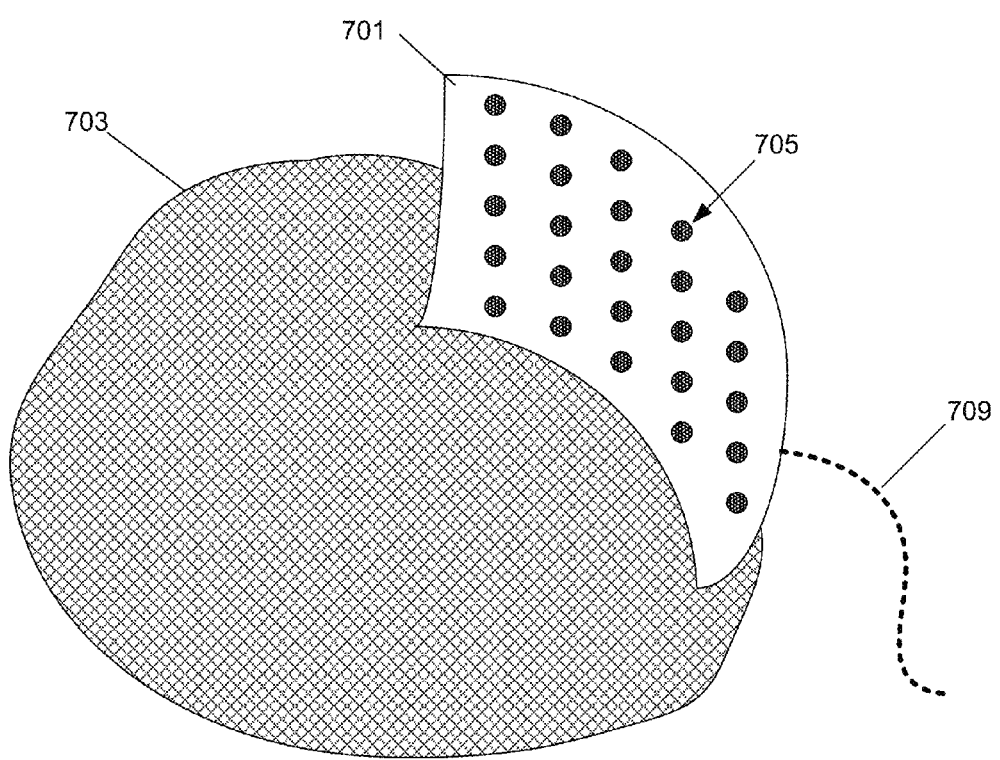
FIG. 7 shows a representative embodiment of a flexible mesh or patch with integrated sensing capabilities at one or more points.

FIG. 7 shows a configuration of the invention where sensing elements are incorporated into a flexible substrate 701. One or more sensing elements 705 are in contact with tissue 703. A medium containing phosphorescent oxygen sensing probes is introduced into tissue 703 and sensing elements 705 illuminate the tissue and monitor the oxygen-dependent quenching of the phosphorescent response. The device may take the form of a patch. It may be applied internally or externally. The patch may be at least partially bioabsorbable. The invention may include an integrated injection system or transdermal delivery system for the sensing medium. One configuration of the patch is for skin flap monitoring or organ transplant assessment. A further configuration is an externally wearable patch to reliably provide tissue oxygenation in a clinical environment that is accurate across a wide range of oxygenations and robust to motion artifact and other sources of error present in pulse oximetry or other traditionally used techniques.

In one embodiment of the invention, the phosphorescent oxygen sensing molecular probes are coupled to a ferromagnetic material and substrate 701 contains an apparatus for manipulating the probe location, or clearance rate. In one configuration, magnets including permanent, switched permanent, or electromagnets are integrated into or otherwise coupled to substrate 701. The magnets attract the probes in the medium to ensure that they remain in the tissue 703 within range of the sensing elements 705. In a further embodiment, the probe is configured with a size appropriate to maintain its location in the tissue for a period of time. The size of the probe is configured such that it remains in tissue 703 without migrating such that sensing may be performed without the need for multiple or continuous injection. The probe may be sized such that it does not migrate, that it clears naturally after a delay, or that it clears rapidly. In a further embodiment, bioabsorbable components are coupled with the probe, such that the probe will have minimal migration while the bioabsorbable components are in place. After a period of time the bioabsorbable material no longer impedes migration or clearing of the probe and it can clear from the tissue 703 and the body. The above described techniques are not limited to use with the embodiment of the patch shown in FIG. 7 and may be applied to other embodiments.

Figure 8:
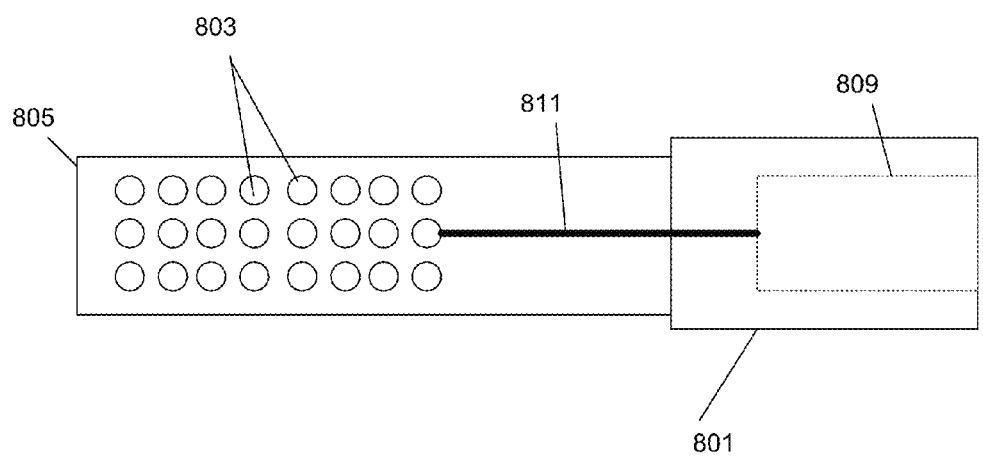
FIG. 8 shows a representative embodiment of an applicator integrated into a surgical instrument, wherein the applicator is a micro needle array.

FIG. 8 shows a microinjection system integrated into surgical instrument 801. Needles 803 protrude from surface 805 into a tissue. In one embodiment, needles 803 are controlled so as to only protrude past surface 805 upon reaching a specific tissue compression pressure. Needle 803 may be a microneedle array. The array may be micromolded. In another configuration, needles 803 are porous needles that deliver the medium along their length into the tissue. In one embodiment, an injection system and vessel 809 are contained in the body of instrument 801 and connected through a tube 811 to needles 803. In an alternate embodiment, a bladder or cavity is collocated with the needle or needle array and used to deliver the medium. In one configuration of the needles 803 are arranged in along a line (straight or curved), and sensing elements are placed along one or both sides of the needles.

Figure 9A:
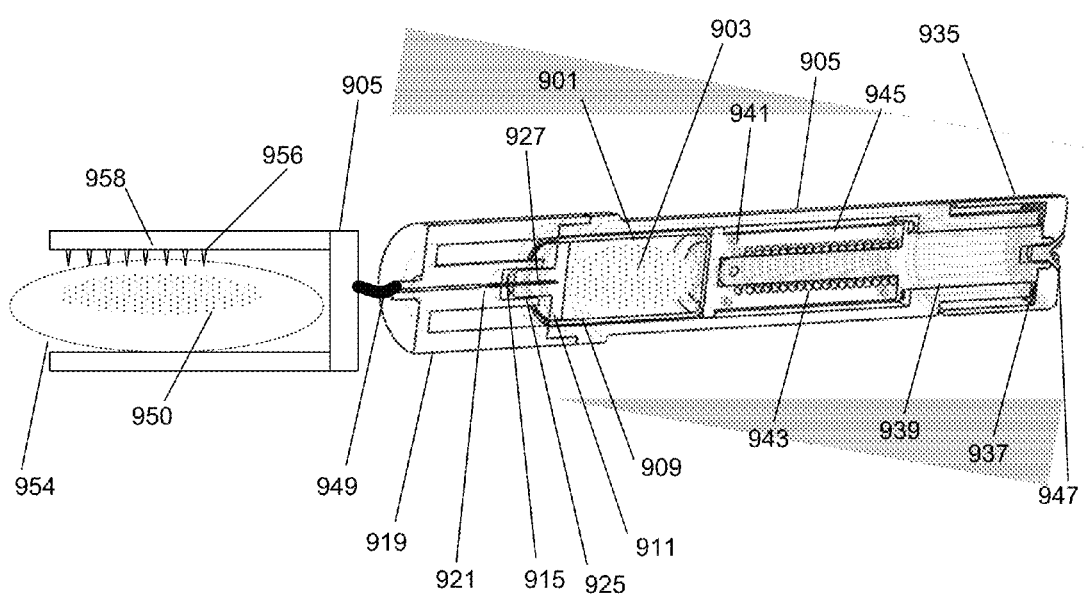
FIG. 9a shows a representative embodiment of an applicator delivery system, wherein a medium is in a removable vessel.
Figure 9B:
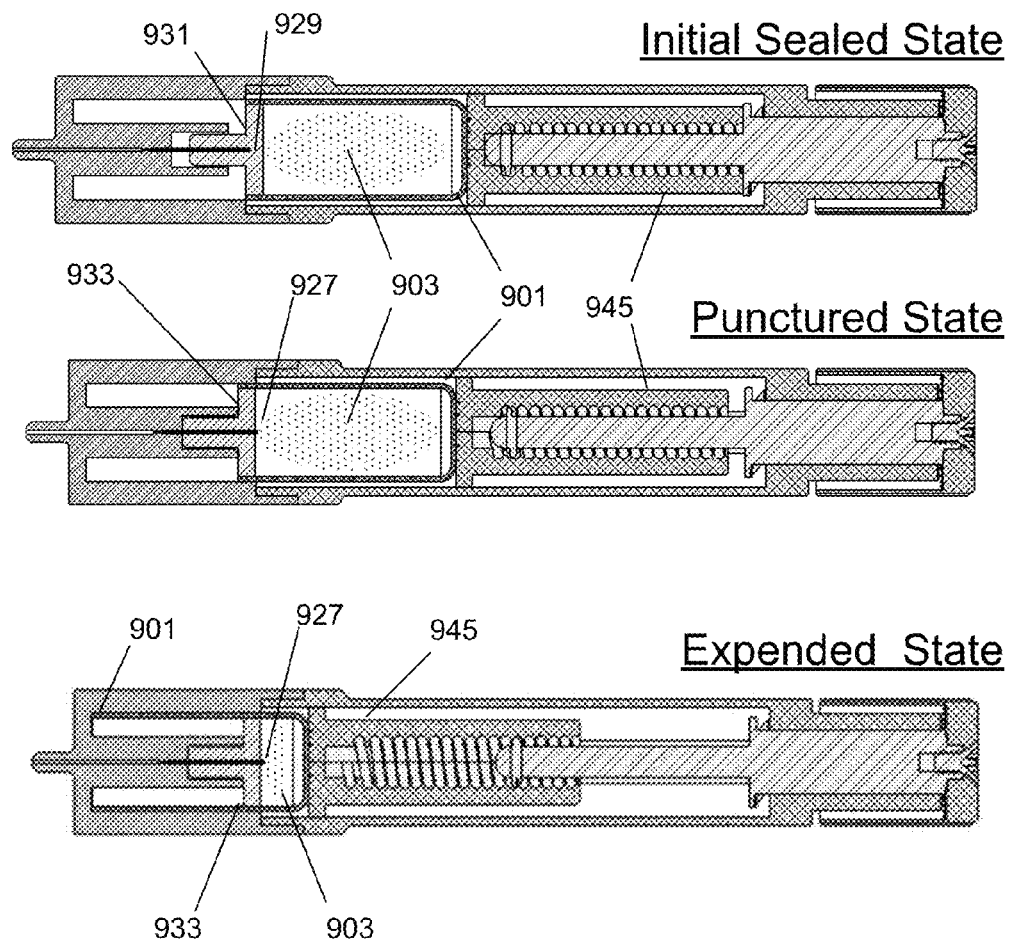
FIG. 9b shows three states of the injector: the initial sealed state, the punctured state, and the expended state.

FIG. 9a details one embodiment of an injection/applicator subsystem configured to deliver medium from apparatus into target biological tissue. A sealed vessel 901 containing medium with light re-emitting molecular probe 903 is incorporated into the body of a surgical instrument 905. The vessel is comprises an outer shell 909, and a plunger 911. The plunger 911 is configured to mate with needle carrier 915. The surgical instrument has a vessel receiver comprising a body 919, and a needle subunit 921. The body 919 of vessel receiver 921 receives the outer shell 909 of the vessel 901. The needle subunit 921 comprises a body 925, a hollow needle 927, and a breakable stop 929. The needle body 925 receives the plunger 911. The initial position 931 of the plunger 911 within needle unit body 925 abuts up against breakable stop 929. The needle 927 is configured such that during initial positioning of the plunger against the breakable stop, the needle is embedded in the plunger, not in contact with the medium. The other end of needle 927 is coupled to a tubing or manifold 949 which conveys medium 903 to needle(s) 956. The user can inject discrete amounts of medium 905 into the tissue 954 through needle(s) 956 at the instruments tissue contacting surface 958 by manipulating knob 935. Knob 935 comprises a ratcheting mechanism 937 allowing for rotation in one direction, at discrete increments. The knob is fixed to actuator rod 939. Rod 939 extends from knob into surgical instrument body 905. The distal end of the rod holds a pin 941. The pin 941 mates with constant or variable pitch threads 943 in pusher unit 945. The pusher unit 945 abuts against vessel shell 901. To inject the medium 903 into the tissue 954, the knob 935 is rotated, which turns rod 939. The subsequent rotation of pin 941 advances the pusher unit 945, and vessel 901 into the vessel receiver 921. Initial rotation of the knob 935 advances the plunger past the breakable stop 929, to final position 933, resulting in communication of needle 927 with medium 903 and priming of needle(s) 956 with medium. Further rotation of knob 935 results in discrete advancement of vessel 901 and ejection of the medium 903 from the vessel 901 in one or more controlled doses shows in tissue 954 as 950. An optional indicator 947 can be incorporated into surgical instrument 905 to indicate state of actuation and dose number. Actuation of the injection system may be either manual or electronically actuated. The medium 903 may be contained in a prefilled vial 901 in the form of a solution or it may be packaged in dried lyophilized form and reconstituted at the time of use. FIG. 9b shows three states of the injector: the initial sealed state, the punctured state, and the expended state.

Figure 10:
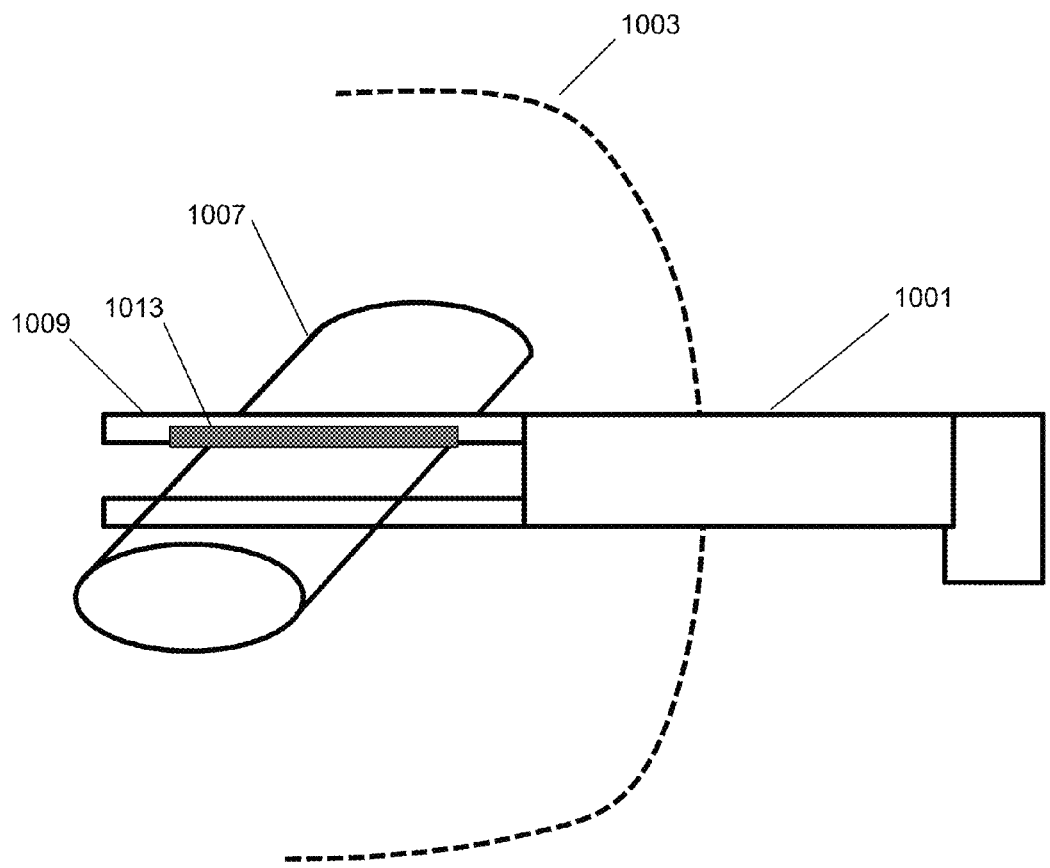
FIG. 10 shows a representative embodiment of an interrogator with capabilities of manipulating an injected probe.

FIG. 10 shows an instrument 1001 inside body 1003, interrogating tissue 1007. Sensing elements are integrated into jaw 1009. A medium is injected into tissue 1007. The medium is ferromagnetic. In one configuration, magnetic components are placed in the tip of instrument 1001 along jaw 1009 to control the flow of the medium. In one configuration, a medium is injected systemically or locally, and magnets 1013 attract the medium or component therein to the sensing elements or slow the flow away from the sensing elements. In another configuration the magnetic components are controllable to manipulate the medium, or particles therein. The magnetic field may be manipulated by moving permanent magnets, switching electro-permanent magnets, adjusting power to electromagnets, or controlling the relative position of the jaws to the tissue and/or medium in the tissue. The magnetically controllable particles or medium may be used in sensing applications, or may be for delivering therapy.

In a configuration of the invention, the probe is coupled with ferromagnetic material such that it is possible to control its delivery via magnetic forces. In another configuration, the probe is coupled with bioabsorbable entities that protrude from the surface. Said entities allow the locally injected probe to remain at or near the injection site for a period of time. After which time, the bioabsorbable entities will dissolve and the probe will be free to clear from the body.

Figure 11:
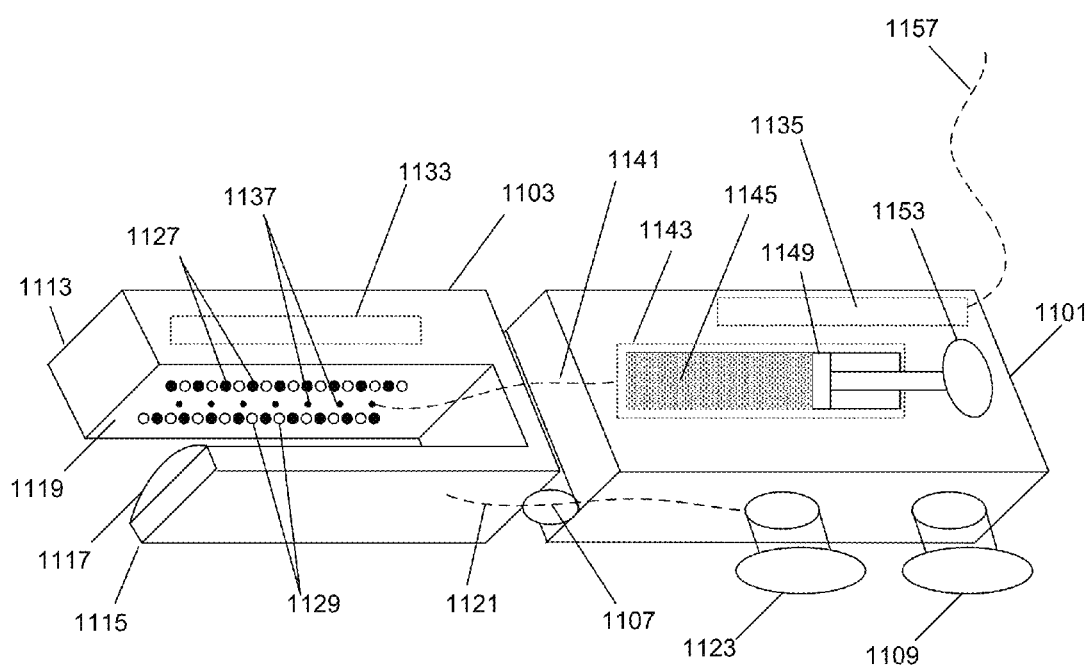
FIG. 11 shows an exemplary representation of a minimally invasive wand interrogator surgical instrument.

FIG. 11 shows an exemplary representation of a minimally invasive wand interrogator instrument. The instrument 1101 has a tissue contacting distal end 1103. In one configuration, the distal end 1103 is articulated with respect to the main body of instrument 1101 at joint 1107. Joint 1107 may have one or more degrees or freedom of articulation. The articulation is controlled from an actuator 1109 on the body of the instrument. Actuator 1109 may be a slider, a knob, a motorized or robotic motion, or an alternative means of controlling the articulation of joint 1107. Joint 1107 may take the form of a rigid hinge or pivot joint or a series of hinged pivots. Alternatively, joint 1107 may be compliant in one or more degrees of freedom. In one configuration, joint 1107 is a flexure joint actuated using shape memory alloy (SMA) or other flexible cables or rods that are controlled by moving a handle 1109.

Distal end 1103 contains two tissue contacting components, upper jaws 1113 and lower jaw 1115. The instrument is manipulated to place a biological tissue (e.g., colonic tissue) between jaws 1113 and 1115. A tissue compression device 1117 is used to compress the tissue against surface 1119 of jaw 1113. Compression device 1117 is capable of ensuring a consistent, standardized pressure along surface 1119. In one embodiment, compression device 1117 is a balloon or bladder which is inflated through tube 1121 through pneumatic or hydraulic means. The device 1117 may incorporate one or more pressure sensors to ensure appropriate pressure is achieved. Pressure may be controlled automatically or manually with actuator or inlet 1123.

One or more sensing elements 1127 and 1129 are integrated into or coupled with face 1119. The sensing elements may include any of the previously described sensor types for measuring physiologic or mechanical properties. In one configuration, the sensing elements include LEDs 1127 and PDs 1129, but may also take the form of other previously described emitters and detectors. In a further embodiment, the LEDs and PDs alternate across and along each of two rows. In one embodiment, the optical sensors use oximetry techniques where one or more wavelengths of light are emitted into the tissue and the absorption properties as detected by the PDs are used to assess tissue oxygenation. In one embodiment, the LEDs are configured to optically excite a phosphorescent probe injected into the tissue and the PDs detect the phosphorescent response in order to assess the oxygen-dependent quenching time. Control electronics 1133 are integrated into the instrument, and may be located in upper jaw 1113 of tip 1103. Additional electronics 1135 may be placed in the main proximal body of instrument. In one configuration, control electronics 1133 in jaw 1113 control the sensing elements and an additional set of control electronics 1135 in the main body include a power source, wired or wireless communication, and user interfaces. User interfaces may include one or more buttons, displays, or audio devices. In one configuration control electronics 1133 manage control of the sensing elements 1127 and 1129 and determine information about the oxygen-dependent quenching time that is used to assess tissue oxygenation at one or more points along surface 1119.

In one embodiment, needles 1137 are used to locally inject a medium containing the phosphorescent oxygen sensing probe. The needles 1137 may be small standard needles, a micromolded needle array, porous needles with individual or a plethora of holes on the side and occluded tips, or other variations for distributing the medium in the tissue. In one configuration multiple needles 1137 and multiple sensing elements 1127 and 1129 provide a distribution of oxygenation in the tissue along face 1119. Needles 1137 may be configured to inject varying amounts to varying depths in the tissue. In one configuration, the sensing instrument is configured to assess a distribution of tissue oxygenation along both sides of layered or tubular tissue. LEDs 1127 sequentially emit two wavelengths, and the time response for each wavelength provides information about the oxygen-dependent quenching at different depths in the tissue as described previously. In one configuration, one or more needles 1137 are inserted laterally along the length of the jaws through the tissue.

The needles 1137 are connected through tube 1141 to reservoir 1143. Tube 1141 may pass through the center axis of articulated joint 1107. Reservoir 1143 contains medium 1145. The medium may contain a phosphorescent oxygen sensing molecular probe. In one embodiment, plunger 1149 is used to inject metered doses of medium 1145 from sealed vessel 1143. The vessel 1143 may contain a specific number or predefined does of the medium 1143. In one embodiment, an actuation device 1153 controls the motion of piston 1149. The actuation device 1153 may be a screw or ratcheting device controlled by the user. It may take the form of a motorized or robotic actuation. The sensing instrument may be used with either locally injected medium, or systemically injected medium. Locally injected medium may be delivered using apparatus associated with the sensing instrument as described, or may be injected using a stand-alone device. In one configuration, a stand-alone device is placed between jaws 1113 and 1115 and the medium is ejected into the tissue. Jaws 1113 and 1115 may be fixed, move in a parallel motion, or close in a hinged motion.

The sensing instrument 1101 may be used as a stand-alone device. In an alternate configuration, a wired or wireless connection 1157 connects to a base station and/or one or more sensing instruments. The instrument may be a minimally invasive surgical instrument, used for traditional open surgical procedures, or configured for external use. The techniques shown in FIG. 11 are directly applicable to other surgical instruments. In one embodiment, instrument 1101 is a surgical stapler anvil. The anvil has a face 1119 that incorporates staple forms. Sensing elements 1127 and 1129 are configured such that they are at the tissue contact face of surface 1119. Needles 1137 may be integrated into the anvil surface 1119, an opposing surface, or an internal cavity. In one configuration, reservoir 1143 is contained inside a cavity in the anvil and a plunger 1149 is actuated as the anvil compresses the tissue against an opposing surface, thus injecting the tissue with the medium 1143 as the stapler is closed and the anvil is compressing the tissue against an opposing surface on the stapler body. In one configuration, the medium 1143 is contained in a reservoir in a separate apparatus which is placed between the anvil and the opposing surface. In this configuration, the reservoir is compressed and ejects the medium into the tissue as the anvil compresses the tissue. This invention includes configurations of the described embodiments wherein an injection system is contained within the sensing device and also configurations wherein the injector is external to the sensing device and may be operated independently.

Figure 12:
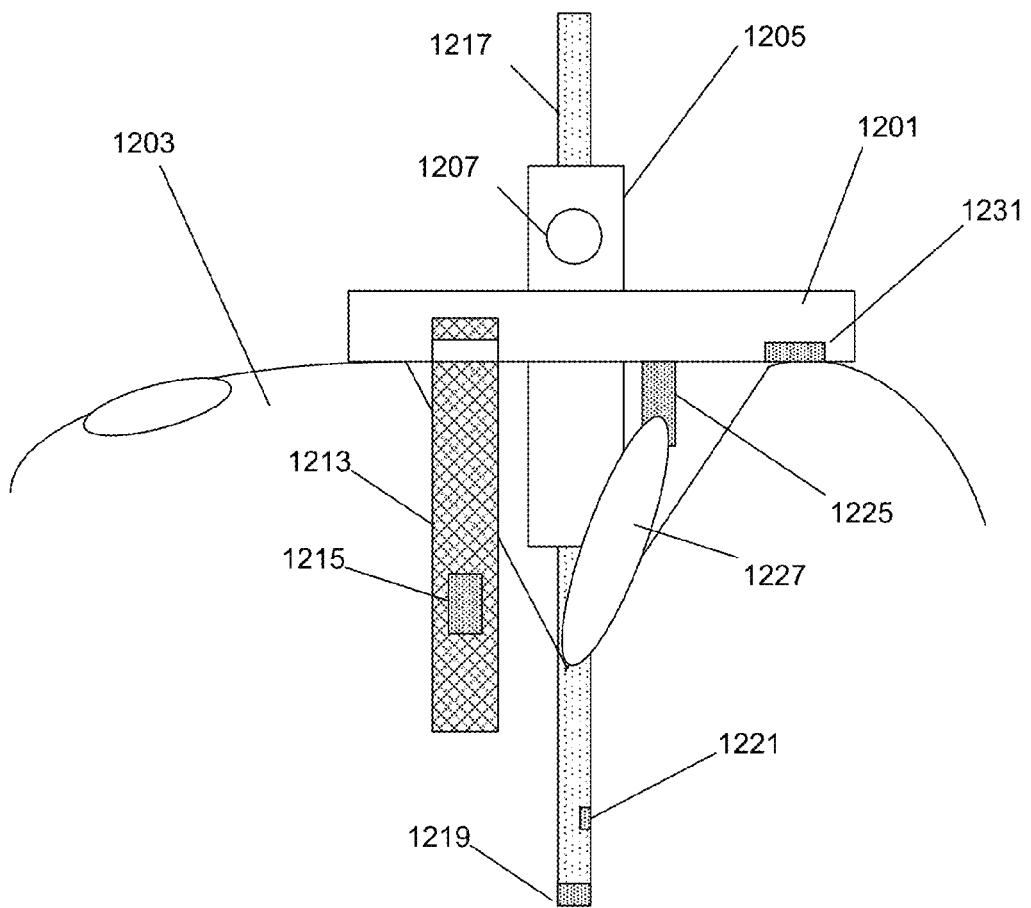
FIG. 12 shows an exemplary embodiment of a medical device incorporating sensing capabilities of the present invention.

FIG. 12 shows one embodiment of the invention, where sensors are coupled with a bite block or other piece of medical equipment 1201 attaching to a patient's face 1203. In one configuration, a bite block 1201 is placed over the mouth of patient 1203. Bite block 1201 has a guide 1205 and clamping device 1207. In one configuration, bite block 1201 is configured to hold an endotracheal (ET) tube 1217. In one configuration, ET Tube 1217 incorporates or is coupled to a sensor 1219 at the distal end. Sensor 1219 may be a single point sensor, a multi-point sensor, or an imaging array. In another configuration, sensor or sensors 1221 are placed along the surface of the ET tube 1217. One or more sensors may be place circumferentially and longitudinally along the tube. It should be noted that tube 1217 is shown as an ET tube as an example, however the present invention includes all such tubes, catheters, cannulas, scopes, needles, and similar rigid and flexible devices for insertion into the mouth or other orifice of the body. Such sensing devices may be used with or without the block 1201. In one embodiment, sensor 1225 operates inside of the patient's mouth. Sensor 1225 may be in contact with tongue 1227. The sensor 1225 may rest on the surface of the tongue 1227, clip to the tongue, or sense sublingually. The sensor 1225 may also be used to sense at other locations in or around the mouth including tongue, cheek, lips, or gums. In a further embodiment, a sensor 1231 is coupled to the block 1201 and in direct contact with the patient 1203. The sensor 1231 may be in contact with the patient's face, cheek, lip, gum, or another external tissue.

It should be noted that these sensing techniques can be applied to other medical devices 1201 attached to patient 1203. In one exemplary configuration, a mask 1201 is placed over the patient. One or more sensors 1231 may be coupled with the mask itself, or one or more sensors 1215 may be coupled with the strap 1213. Similarly, sensors 1215 may reside in a band or strap that may or may not contain another medical device, and may be affixed to the head or other part of the body. In one configuration, a sensor may be used to determine tissue oxygenation or other properties at the skin surface, or at a depth below the surface. Such sensing may include assessing tissue oxygenation or other properties of tissue within the skull. A further exemplary configuration is a wearable strap or band 1213 with one or more sensors 1215 coupled with it. In one embodiment, one or more of sensors 1215, 1219, 1221, and 1231 are configured to sense oxygenation through the use of phosphorescent oxygen sensing probes as described herein. In a further configuration, injection devices to introduce a medium containing the probe may be coupled with the sensors. In an alternate configuration, the probe is injected locally by other means or systemically. The described techniques for manipulating the position or flow of the probe may be applied with this device, as with other devices presented in the invention. The sensors 1215, 1219, 1221, and 1231 may be configured to sense oxygenation by oxygen-dependent quenching of a phosphorescent probe, tissue spectroscopy, pulse oximetry, or other means, and/or may be configured to sense blood flow or perfusion, and/or may be configured to sense mechanical properties of the tissue or tissue sensor-interaction. In one embodiment the device takes the form of a bite block or indwelling line/tube such as an intracranial, endotracheal, oro/naso gastric tube, venous catheter, arterial catheter, chest tube, feeding tube, urinary catheter, or rectal tube. The sensor elements are positioned on said tube in a manner such that they contact biological tissue. Phosphorescent medium is either systemically or locally injected into subject tissue. Previously described techniques for injection as well as maintaining the location of the medium in the vicinity of the sensor may be utilized with the configurations described herein.

Figure 13A:
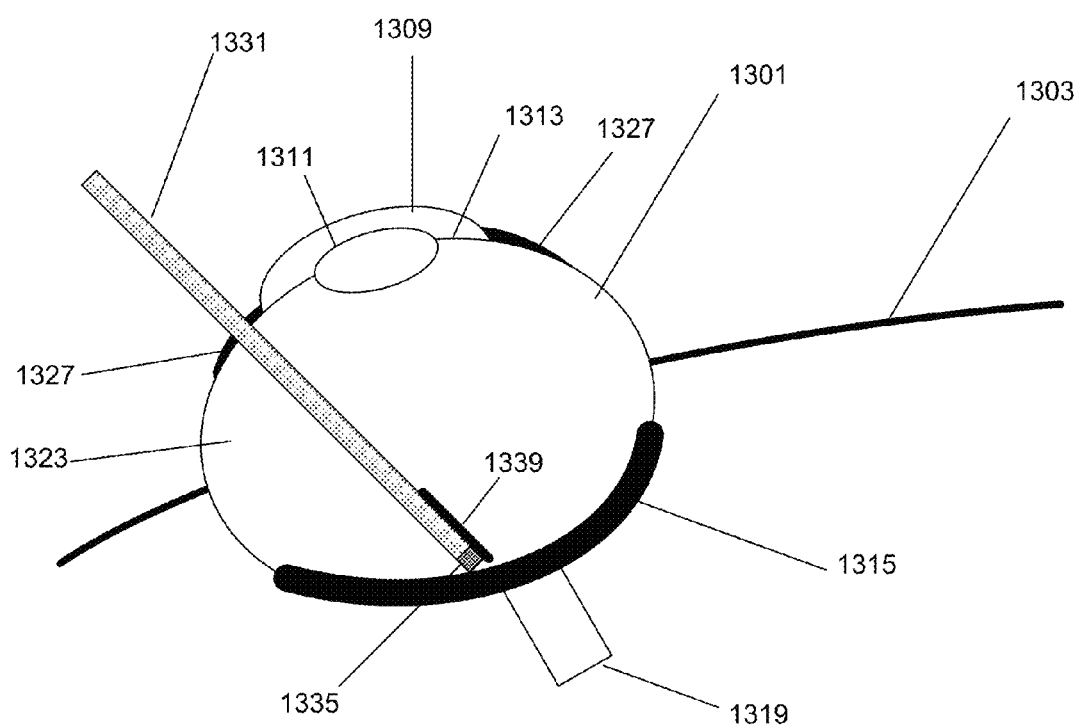
FIG. 13a shows a representative embodiment of minimally invasive oxygen mapping system for ophthalmic surgery with an integrated applicator.

FIG. 13a shows an embodiment of the present invention configured for ophthalmologic applications, such as retinal surgery. The figure shows eye 1301 of patient 1303 with cornea 1309, lens 1311, and iris 1313. In one embodiment, a surgical instrument or imaging device 1331 is used to assess oxygenation or perfusion in retina 1315 or at optic nerve 1319. In one configuration, instrument enters the vitreous 1323 of the eye through the sclera 1327. The present invention describes a sensing instrument that can be inserted into the eye through the sclera 1327, or through another entry point and is capable of sensing oxygenation, perfusion, or other physiologic or mechanical properties within the eye 1301. In one configuration, instrument 1331 includes a sensor or sensing element 1335 at the distal end of the instrument. The sensor 1335 may come in direct contact with the retina 1315 (or other feature), or may be used at a distance from the surface. Sensor 1335 may be a single point sensor, an imaging system such as a camera system, or a fiberoptic or other light transmission bundle connecting to an external imaging system. The previously described mapping and imaging techniques may be used. In one configuration a micro camera system is utilized at the tip 1335 of the instrument. In another configuration, light guides such as an optical fiber bundle or other means of light transmission such as GRIN lenses are utilized to couple tip 1335 with a remote detector distal to instrument 1331 such as a camera. Sensor 1335 may be used to assess tissue oxygenation at a single location, swept to generate a map of tissue oxygenation, or may directly generate a 2D map.

In one configuration, an injector or injection system 1339 is used to inject a medium containing an oxygen sensing molecular probe into the retina 1315 or other tissue. In other configurations, an external injector provides a local injection of the probe or a systemic injection is performed to infuse the tissue with the oxygen sensing probe. The instrument 1331 may be manipulated manually, or it may be moved using a robots or other externally controlled means. In one embodiment, instrument 1331 is manipulated to scan sensor 1335 across the tissue surface to determine the oxygenation and/or other properties at multiple points. In a further configuration, by manipulating the tool, a 2D or 3D oxygenation map of the retina 1315 is generated. The map may be fused with camera-based imaging to generate an overlay of oxygenation or flow on a video steam or captured still image. In one configuration, traditional endoscopy images are collected along with quantitative oxygen maps and are visualized together. In another embodiment, the imaging device does not enter the vitreous 1323, and rather images the oxygenation in the eye through lens 1311. The sensing instrument may be a stand-alone device, used in conjunction with imaging or surgical equipment such as an endoscope, or integrated into or coupled with such imaging or surgical equipment. In a further embodiment, sensor 1335 of instrument 1331 is configured to image beyond the retina to a point within the skull, including the brain. The described sensor 1335 may be configured to assess tissue oxygenation based on oxygen-dependent quenching of a molecular probe as described herein. It may further incorporate other optical or mechanical sensing techniques as described elsewhere in this disclosure.

Figure 13B:
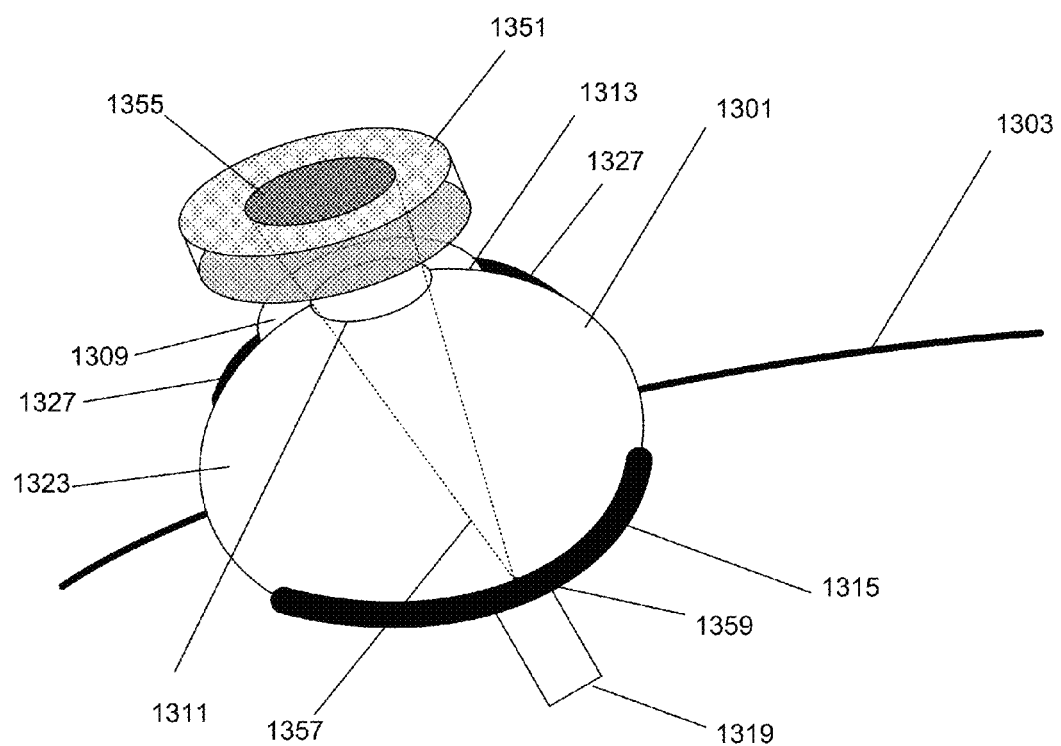
FIG. 13b shows a representative embodiment of an oxygen mapping system as applied to retinal imaging.

FIG. 13b shows an embodiment of the invention where the sensing device 1351, or component thereof, is external to the eye 1301. The sensing device 1351 rests on or is external to the cornea 1309 for non-invasive sensing of oxygenation in the eye. In one configuration, sensing device 1351 takes the form of a contact lens or other similar object substantially made of hydrogel or similar material and rests on cornea 1309. In another configuration, sensing device 1351 is a patch that rests over the eye 1301 and may rest on face 1303. In an alternate configuration, the sensing device 1351 is externally mounted. One example of an externally mounted device 1351 is coupled to or incorporated into a surgical microscope. In another embodiment, the sensing device 1351 is mounted to or incorporated into a pair of eye glasses, goggles, or eyewear. In another embodiment, sensor 1351 is configured to act as a biometric device interrogating retina 1315, or the optic nerve 1319 to aid in identification of an individual.

Sensing device contains one or more sensing elements 1355. The sensing elements may be integral parts of sensing device 1351, or connected via optical fibers, wires, wireless, or other means. In one embodiment, the sensing device is configured to assess oxygenation through optical means of monitoring an injected molecular phosphorescent probe that has oxygen-dependent phosphorescent quenching characteristics. In one configuration the sensing elements 1355 emit one or more wavelengths of light 1357 through the eye's lens 1311 such that it focuses on a point 1359, such as the fovea, on the optic nerve 1319. One application of the invention is to assess oxygenation of the optic nerve, as a proxy for brain oxygenation. In another application, the invention is used to determine a map of oxygenation at and near the optic nerve 1319 and/or on the retina 1315. The exemplary embodiment of an oxygen imaging system (i.e. oxygen mapping system) shown in FIG. 3 is only an example configuration and this approach may be utilized in other configurations for other organ systems. In a further embodiment, this approach is utilized for assessing oxygenation of gastrointestinal tissue. It may be further utilized in the previously described approach to measure oxygenation before, during, and after CRC surgery.

Accordingly, one embodiment includes a surgical device for sensing tissue oxygenation based upon oxygen-dependent quenching of phosphorescent oxygen sensing probe.

Another embodiment includes a minimally invasive surgical device configured to sense oxygenation of a tissue, wherein the sensing is based upon oxygen-dependent quenching of a phosphorescent oxygen sensing probe, wherein the surgical device contains a mechanism for ensuring consistent compression pressure the tissue.

Another embodiment includes a surgical instrument for manipulating biological tissue, wherein the instrument incorporates an injection system configured to deliver a medium consisting in part of oxygen sensing probes to the tissue, wherein the instrument further incorporates a sensing system configured to detect the optical response the oxygen sensing probes in the tissue.

Another embodiment includes a surgical instrument for manipulating biological tissue, wherein the instrument incorporates a microneedle array configured to inject a medium into the tissue.

Another embodiment includes a surgical instrument for manipulation biological tissue, wherein the instrument incorporates a microinjection system into the body of the instrument, wherein the instrument further comprises one or more needles, wherein the microinjection system controls injection of a medium into the tissue through the one or more needles.

Another embodiment includes a surgical instrument for manipulating biological tissue, wherein the instrument comprises a means for producing constant compression pressure of the tissue against a surface of the instrument.

Another embodiment includes a method for manipulating an injectable probe, wherein the probe incorporates ferromagnetic material, and wherein a surgical instrument incorporates magnets to attract and retain the molecule.

Another embodiment includes a surgical instrument incorporating a means for injection of medium into tissue, and further incorporates a means for manipulating the location of the medium in the tissue after injection.

Another embodiment includes a method for maintaining the position of a locally injected probe at the injection site in a tissue for a period of time, wherein bioabsorbable entities are incorporated into the probes structure, wherein the bioabsorbable entities detach from the probe and enable clearance from the body.

Another embodiment includes a surgical instrument comprising a high speed imaging system, wherein the imaging system is configured to provide data to generate maps of tissue oxygenation based upon phosphorescent optical response of an injectable oxygen sensing probe.

Another embodiment includes a surgical instrument for eye surgery comprising an imaging system, wherein the imaging system is configured to provide data to generate maps of tissue oxygenation based upon phosphorescent quenching time of an oxygen sensing probe.

Another embodiment includes a method of sensing and discriminating oxygenation in two or more layers of tissue, wherein oxygenation is sensed based on phosphorescent quenching time of a phosphorescent oxygen sensing probe, wherein the probe has multiple absorption wavelengths that have different tissue absorption properties, wherein the oxygen is discriminated based on the phosphorescent response due to multiple emission wavelengths.

Another embodiment includes a surgical system comprising a surgical instrument configured to assess tissue oxygenation, and further comprising a sensing device configured to assess tissue oxygenation that couples to a surgical stapler, wherein both devices are configured to assess oxygenation of tissue using an injectable phosphorescent oxygen sensing probe, wherein the system is configured to provide information to guide a surgical procedure.

Another embodiment includes a surgical instrument comprising a plurality of sensing elements, wherein at least the instrument is configured to assess tissue oxygenation based on the quenching time of an injectable phosphorescent probe, wherein the instrument is further configured to sense at least one of tissue oxygenation, blood oxygenation, pulse rate, pulse presence, pulse rhythm, tissue perfusion, staple gap, compression force, tissue interaction force, fluorescence, tissue electrical impedance, tissue electrical activity, pH, concentration of cellular respiration metabolites, electromyography, temperature, fluid flow rate, fluid flow volume, tissue pressure, blood pressure, biomarkers, radiotracers, immunologic characteristics, biochemical characteristics, nerve activity, an evoked potential, oxygen delivery, oxygen utilization, tissue characterization, tissue general health, tissue flow dynamics, tissue chemical composition, tissue immunologic activity, tissue pathogen concentration, tissue water content, blood hemoglobin content, tissue chromophore content, tissue neoplastic cell content and tissue dysplastic cell content.

Another embodiment includes a surgical instrument configured to assess tissue oxygenation based on the quenching time of an injectable phosphorescent probe, wherein the instrument is communicatively coupled via a wireless connection to a base station.

Another embodiment includes a sensing surgical stapler anvil, wherein the sensing anvil is configured to assess oxygenation of tissue at the site of an anastomosis, wherein the assessment of oxygenation is based on the quenching time of an injectable phosphorescent probe.

Another embodiment includes an adjunct to a surgical stapler incorporating at least one sensor configured to assess the oxygenation of a tissue based on the quenching time of an injectable phosphorescent probe, wherein the adjunct operates independently of the stapler; wherein adjunct is optionally coupled to the stapler.

Another embodiment includes a medical device configured for sensing tissue oxygenation, the device comprising at least one sensor, wherein at least one sensor of the device detects the optical response of an oxygen sensing probe.

The oxygen sensing probe has a phosphorescent optical response, wherein the phosphorescent lifetime of the optical response is responsive to oxygen-dependent quenching.

The medical device may be a surgical instrument for manipulating biological tissue.

The medical device may be a minimally invasive surgical instrument.

The surgical instrument further comprises a mechanism for ensuring consistent compression pressure on the tissue.

The surgical instrument may further comprises an injection system configured to deliver a medium to the tissue, wherein the medium includes the oxygen sensing probes.

The injection system may comprise a plethora of microneedles.

The surgical instrument may be a surgical stapler or component thereof.

The surgical instrument may be a surgical stapler anvil with integrated oxygen sensing capabilities.

The medical device may be patch with integrated oxygen sensing capabilities.

The patch may be fully or partially bioabsorbable.

The medical device may be communicatively coupled via a wireless connection to a base station.

A surgical stapler anvil may be configured to assess oxygenation of a biological tissue at the site of an anastomosis, wherein the assessment of oxygenation is based on oxygen-dependent quenching time of an injectable phosphorescent probe.

An adjunct to a surgical stapler incorporating at least one sensor may be configured to assess oxygenation of a biological tissue, wherein the assessment of oxygenation is based on oxygen-dependent quenching time of an injectable phosphorescent probe, wherein the adjunct operates independently of the stapler; wherein adjunct is optionally coupled to the stapler.

A surgical system may include a surgical instrument configured to assess oxygenation of a biological tissue, and a sensing device configured to assess tissue oxygenation that couples to a surgical stapler. The devices are configured to assess oxygenation of biological tissue using an injectable phosphorescent oxygen sensing probe.

The surgical system may be further configured to provide information to guide a surgical procedure.

An imaging system may be configured to provide a 2D map of tissue oxygenation, wherein the imaging system generates the map responsive to oxygen-dependent quenching of the phosphorescent response of oxygen sensitive molecules.

The imaging system may be incorporated into a surgical instrument.

The surgical instrument may be configured for ophthalmic surgery, wherein the instrument provides an oxygenation map of the retina.

The surgical instrument may be configured to provide an oxygen map of gastrointestinal tissue.

The surgical instrument may be configured to assist in analysis of a target tissue, wherein analysis is performed for at least one of before, during, and after creation of an anastomosis.

A surgical instrument may manipulate ipulating biological tissue, wherein the instrument incorporates a microinjection system into the body of the instrument, wherein the instrument further comprises one or more needles, wherein the microinjection system controls injection of a medium into the tissue through the one or more needles.

A surgical instrument may manipulate biological tissue, wherein the instrument comprises a means for producing constant compression pressure of the tissue against a surface of the instrument.

A method may manipulate an injectable probe, wherein the probe incorporates ferromagnetic material, and wherein a surgical instrument incorporates magnets to attract and retain the molecule.

A surgical instrument may incorporate a means for injection of medium into tissue, and further incorporates a means for manipulating the location of the medium in the tissue after injection.

A method may maintain the position of a locally injected probe at the injection site in a tissue for a period of time, wherein bioabsorbable entities are incorporated into the probes structure, wherein the bioabsorbable entities detach from the probe and enable clearance from the body.

A method of sensing and discriminating oxygenation in two or more layers of tissue may be provided, wherein oxygenation is sensed based on phosphorescent quenching time of a phosphorescent oxygen sensing probe, wherein the probe has multiple absorption wavelengths that have different tissue absorption properties, wherein the oxygen is discriminated based on the phosphorescent response due to multiple emission wavelengths.

A surgical instrument may comprise a plurality of sensing elements, wherein at least the instrument is configured to assess tissue oxygenation based on the quenching time of an injectable phosphorescent probe, wherein the instrument is further configured to sense at least one of tissue oxygenation, blood oxygenation, pulse rate, pulse presence, pulse rhythm, tissue perfusion, fluorescence, tissue electrical impedance, tissue electrical activity, pH, concentration of cellular respiration metabolites, electromyography, temperature, fluid flow rate, fluid flow volume, tissue pressure, blood pressure, biomarkers, radiotracers, immunologic characteristics, biochemical characteristics, nerve activity, an evoked potential, oxygen delivery, oxygen utilization, tissue characterization, tissue general health, tissue flow dynamics, tissue chemical composition, tissue immunologic activity, tissue pathogen concentration, tissue water content, blood hemoglobin content, tissue chromophore content, tissue neoplastic cell content and tissue dysplastic cell content.

The embodiments described above demonstrate how oxygen sensitive probes can be utilized with surgical instruments incorporating sensors. These embodiments are meant as illustrative purposes. The described sensing instruments and approaches can be adapted to provide the described functionalities for other surgical instruments or medical devices. Further, the techniques discussed should not be construed to be limited to use only with phosphorescent oxygen sensing probes. Further still, all references to phosphorescence or fluorescence more broadly may be applied to all light-remitting phenomenon.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A monitoring device configured to map oxygenation of a tissue containing an injectable, light re-emitting probe, the monitoring device comprising:
 at least one optical emitter that is configured to excite the injectable, light re-emitting probe;
 at least one optical detector configured to receive the re-emitted light from the probe;
 a signal processor that is configured to resolve the tissue oxygenation at multiple points based on an oxygen-dependent optical response of light emitted by the injectable, light re-emitting probe to generate an oxygen map; and a temperature sensor that is configured to detect a temperature of the tissue,
wherein the signal processor is configured to receive temperature data from the temperature sensor to calibrate resolving the tissue oxygenation based on the temperature dependence of the oxygen-dependent optical response.

2. The monitoring device according to claim 1, further comprising at least one injector configured to inject a medium into target tissue, the medium containing the light re-emitting probe.

3. The monitoring device according to claim 1, wherein the optical detector is at least one of a CCD array, a CMOS image sensor and a camera.

4. The monitoring device according to claim 1, wherein the monitoring device is an endoscopic instrument.

5. The monitoring device according to claim 1, wherein the monitoring device is ingestible.

6. The monitoring device according to claim 1, wherein the monitoring device is a surgical instrument.

7. The monitoring device according to claim 6, further comprising an applicator configured to provide a target tissue with a medium, the medium containing the light re-emitting probe.

8. The monitoring device according to claim 6, wherein the signal processor is configured to resolve the tissue oxygenation based on a lifetime of the re-emitted light.

9. The monitoring device according to claim 6, wherein the surgical instrument is a surgical stapler anvil.

10. The monitoring device according to claim 7, wherein the applicator is at least one injector that is configured to inject the medium into the target tissue.

11. The monitoring device according to claim 1, further comprising an interrogator instrument that is configured to interrogate the tissue.

12. The monitoring device according to claim 1, wherein the signal processor makes a determination of an operation success based on the resolution of the tissue oxygenation.

13. The monitoring device according to claim 1, further comprising at least one sensor configured to monitor interaction forces of at least one of compression pressure and tissue tension of the tissue.

14. The monitoring device according to claim 1, wherein the probe is a phosphorescent probe that has multiple absorption wavelengths.

15. The monitoring device according to claim 1, wherein the monitoring device is communicatively coupled to a base station.

16. The monitoring device of claim 1, further comprising:
a flexible substrate having a tissue interfacing surface, the tissue interfacing surface containing (1) at least one optical emitter that is configured to excite the light re-emitting probe, and (2) at least one optical detector configured to receive the re-emitted light from the probe; and
a signal processor that is configured to resolve the tissue oxygenation based on the received light.

17. The monitoring device according to claim 16, wherein the flexible substrate is configured to be one or more of: (1) affixed to skin and (2) affixed to an internal tissue.

18. The monitoring device according to claim 16, wherein the monitoring device is at least partially bioabsorbable.

19. The monitoring device of claim 1, wherein the calibrating is based on calibration parameters of the probe.

20. The monitoring device of claim 19, wherein the calibration parameters of the probe comprise a quenching constant (kq) and a phosphorescence lifetime in an absence of oxygen ($\tau 0$).

* * * * *